(12) United States Patent
Liu et al.

(10) Patent No.: US 12,396,694 B2
(45) Date of Patent: Aug. 26, 2025

(54) STATIONARY DETAIL IMAGING IN CONE BEAM BREAST COMPUTED TOMOGRAPHY

(71) Applicant: Koning Corporation, Norcross, GA (US)

(72) Inventors: Shaohua Liu, Atlanta, GA (US); Ruola Ning, Atlanta, GA (US)

(73) Assignee: KONING CORPORATION, Norcross, GA (US)

(*) Notice: Subject to any disclaimer, the term of this patent is extended or adjusted under 35 U.S.C. 154(b) by 0 days.

(21) Appl. No.: 18/914,216

(22) Filed: Oct. 13, 2024

(65) Prior Publication Data

US 2025/0032076 A1    Jan. 30, 2025

Related U.S. Application Data

(63) Continuation of application No. PCT/US2023/018369, filed on Apr. 12, 2023.

(60) Provisional application No. 63/331,153, filed on Apr. 14, 2022, provisional application No. 63/401,475, filed on Aug. 26, 2022, provisional application No. 63/401,493, filed on Aug. 26, 2022, provisional application No. 63/401,513, filed on Aug. 26, 2022, provisional application No. 63/401,546, filed on Aug. 26, 2022, provisional application No. 63/401,548, filed on Aug. 26, 2022, provisional application No. 63/430,571, filed on Dec. 6, 2022.

(51) Int. Cl.
| | |
|---|---|
| *A61B 6/00* | (2024.01) |
| *A61B 6/03* | (2006.01) |
| *A61B 6/04* | (2006.01) |
| *A61B 6/40* | (2024.01) |
| *A61B 6/50* | (2024.01) |
| *A61B 8/08* | (2006.01) |
| *G06T 7/00* | (2017.01) |

(52) U.S. Cl.
CPC .............. *A61B 6/502* (2013.01); *A61B 6/032* (2013.01); *A61B 6/035* (2013.01); *A61B 6/0435* (2013.01); *A61B 6/0478* (2013.01); *A61B 6/0487* (2020.08); *A61B 6/4085* (2013.01); *A61B 8/0825* (2013.01); *G06T 7/00* (2013.01); *G06T 2207/30068* (2013.01)

(58) Field of Classification Search
CPC ............................... A61B 6/502; A61B 6/032
See application file for complete search history.

(56) References Cited

U.S. PATENT DOCUMENTS

| | | | |
|---|---|---|---|
| 5,506,877 | A | 4/1996 | Niklason et al. |
| 6,987,831 | B2 | 1/2006 | Ning |
| 10,772,584 | B2 | 9/2020 | Defreitas et al. |
| 2009/0171244 | A1 | 7/2009 | Ning et al. |
| 2010/0067648 | A1* | 3/2010 | Kojima .................. A61B 6/502 378/11 |
| 2017/0231588 | A1 | 8/2017 | Shores et al. |
| 2021/0219933 | A1 | 7/2021 | Boone et al. |

\* cited by examiner

*Primary Examiner* — Dani Fox
(74) *Attorney, Agent, or Firm* — Bergman LLC; Michael Bergman

(57) ABSTRACT

A cone beam breast computer tomographic imaging system includes a subsystem for stationary scanning such that the same system can produce a cone beam breast computer tomographic image and a 2D stationary scan image.

14 Claims, 23 Drawing Sheets

STATIONARY DETAIL IMAGING IN CONE BEAM BREAST COMPUTED TOMOGRAPHY

CROSS-REFERENCE TO RELATED APPLICATIONS

The present application is a continuation of PCT patent application PCT/US2023/018369 filed on Apr. 12, 2023, which claims the benefit of provisional patent applications OMNIBUS DISCLOSURE, set forth in an application for Letters Patent of the United States already filed on Apr. 14, 2022 as U.S. Provisional Application No. 63/331,153, and FIXTURING AND SUPPORT FOR MEDICAL IMAGING, set forth in an application for Letters Patent of the United States already filed on Aug. 26, 2022 as U.S. Provisional Application No. 63/401,475, and ERGONOMIC IMPROVEMENTS IN CONE BEAM BREAST COMPUTED TOMOGRAPHY, set forth in an application for Letters Patent of the United States already filed on Aug. 26, 2022 as U.S. Provisional Application No. 63/401,493, and STATIONARY DETAIL IMAGING IN CONE BEAM BREAST COMPUTED TOMOGRAPHY, set forth in an application for Letters Patent of the United States already filed on Aug. 26, 2022 as U.S. Provisional Application No. 63/401,513, and CONE BEAM BREAST COMPUTED TOMOGRAPHY WITH PATIENT SUPPORT SUBSYSTEM, set forth in an application for Letters Patent of the United States already filed on Aug. 26, 2022 as U.S. Provisional Application No. 63/401,546, and, CONE BEAM BREAST COMPUTED TOMOGRAPHY WITH PIVOTAL GANTRY SUBSYSTEM, set forth in an application for Letters Patent of the United States already filed on Aug. 26, 2022 as U.S. Provisional Application No. 63/401,548, and ULTRASONIC HYBRID IMAGING IN CONE BEAM BREAST COMPUTED TOMOGRAPHY, set forth in an application for Letters Patent of the United States already filed on Dec. 6, 2022 as U.S. Provisional Application No. 63/430,571, the disclosures of all of which are herewith incorporated by reference in their entireties.

FIELD OF THE INVENTION

The present invention relates to the field of cone beam tomographic imaging, and in particular to image detail improvement in cone beam breast tomographic imaging.

SUMMARY

According to the National Cancer Institute, one out of eight women will be diagnosed with breast cancer in her lifetime. And while a reduction in mortality from breast cancer is evident in published reports, each year 40,000 women will die of the disease.

The optimal breast imaging technique detects tumor masses when they are small, preferably less than 10 mm in diameter. It is reported that 93% of women with mammographically detected invasive breast carcinoma 1-10 mm have a 16-year survival rate. In addition, as the diameter of the tumor at detection decreases, the probability of metastasis declines sharply. If a breast tumor is detected when it is 10 mm or less, the probability of metastasis will be equal to 7.31%. If a 4 mm carcinoma is detected, the metastatic probability will be decreased by more than a factor of 10, to 0.617%.

Although mammography, which on average can detect cancers about 12 mm in size, is the most effective tool for the early detection of breast cancer currently available, mammography has relatively low sensitivity to small breast cancers (under several millimeters). Specificity and the positive predictive value of mammography remain limited owing to structure and tissue overlap. The limited sensitivity and specificity in breast cancer detection of mammography are due to its poor contrast detectability, which is common for all types of projection imaging techniques (projection imaging can only have up to 10% contrast detectability), and mammography initially detects only 65-70% of breast cancers. The sensitivity of mammography is further reduced to as low as 30% in the dense breast. Digital mammography (DM) was developed to try to overcome the limitations inherent in screen-film mammography (SFM) by providing improved contrast resolution and digital image processing; however, a large-scale clinical trial, the Digital Mammographic Imaging Screening Trial (DMIST), showed that the rates of false positives for DM and SFM were the same.

The relatively low specificity of mammography leads to biopsy for indeterminate cases, despite the disadvantages of added cost and the stress it imposes on patients. Nearly 80% of the over one million breast biopsies performed annually in the U.S. to evaluate suspicious mammographic findings are benign, burdening patients with excessive anxiety and the healthcare system with tremendous cost. There is a need for more accurate characterization of breast lesions in order to reduce the biopsy rate and the false-positive rate of pre-biopsy mammograms.

To address the mammography limitations as indicated above, one of the inventors has previously developed a cone beam breast CT (CBBCT). Briefly, the major features of CBBCT include a horizontal, ergonomically designed patient table with a modular insert to optimize coverage of the uncompressed breast, including the chest wall; wide openings (1 m) on each side of the patient table for easy access to the breast for positioning and potentially good access for imaging-guided biopsy and other procedures without significantly changing the basic platform; and slip-ring technology that facilitates efficient dynamic contrast imaging studies and angiogenesis imaging in the future.

The results of phantom studies indicate that CBBCT can achieve a spatial resolution up to about 2.8 lp/mm, allowing detection of a 2 mm carcinoma and microcalcifications about 0.2 mm in size for an average size breast (about 13 cm in diameter at the chest wall) with a total dose of about 5 mGy. This dose is less than that of a single mammography exam, assuming two views are required for each breast. The image quality of CBBCT for visualizing breast tissues, breast tumors and calcifications is excellent, and coverage of the breast, including the chest wall region, is at least equivalent to mammography. Visualization of major blood vessels is very good without using a contrast agent. Accordingly, CBBCT offers significant improvement in detecting and biopsying suspected lesions in a patient.

Additional improvements in CBBCT imaging offer the potential to expand on these benefits. Among these improvements are technical improvements, and methods and apparatus that facilitate presentation of the patient to the CBBCT system. Among these, the addition of stationary scan techniques to CBBCT imaging offers the potential to significantly enhance image resolution and improve the detection of fine features including calcification within a breast being imaged.

In sum, CBBCT offers the ability to visualize a breast in remarkable detail in three dimensions, and to identify potential lesions, calcifications, vascular abnormality and other indicia of disease, and a comparatively low cost in radiation risk and patient discomfort. The inventors have understood, that beyond these advantages, CBBCT imaging will be substantially improved by an ability to align a CBBCT imaging system along a selected axis, and to image a breast, or a selected region of that breast, with substantially increased clarity and resolution. In particular, a system in which multiple such "stationary scans" can be readily produced can offer significantly increased benefits including improved diagnostic effectiveness.

In conventional mammography breast imaging is preceded by insertion of a patient's breast into a fixturing apparatus that significantly compresses breast tissue in a direction transverse to a breast longitudinal axis. Patients widely report physical and psychological discomfort related to this compression, and studies have shown that this discomfort is a contributing factor to low rates of screening and diagnostic mammography among patients generally and, in particular, among some ethnic and cultural populations.

Moreover, the breast compression associated with mammography can result in a displacement of breast tissue that makes the later localization of features such as lesions and calcifications, for purposes of biopsy and lumpectomy procedures, more difficult.

In current practice, a patient undergoing CBBCT lies prone on a table. A subject breast is disposed downward through an aperture in an upper surface of the table, depending from the chest wall into an imaging chamber disposed under the table. The position of the breast within the imaging chamber is maintained by stasis of the patient as the patient lies on an upper surface of the table.

An imaging apparatus is coupled to a mobile gantry which is supported on a bearing device for rotation about an axis of rotation. The axis of rotation is disposed in a generally vertical orientation and passes through the aperture in the upper surface of the table. Preferably, an approximate centroid of the breast to be imaged is arranged such that the axis of rotation passes through the approximate centroid.

During imaging, the mobile gantry rotates around the axis of rotation, bringing the imaging apparatus through at least a portion of a circular path. As it traverses this path, the imaging apparatus emits a series of x-ray pulses and captures corresponding image data which is processed to prepare a tomographic model of the breast.

In existing CBBCT systems, the breast hangs freely through an aperture in a patient table disposed in a generally horizontal orientation within the imaging chamber.

The inventors of the present invention having given long and careful consideration to the improvement of CBBCT imaging (and, in particular, to questions of CBBCT image enhancement), have developed new and useful systems, apparatus and methods that represent a substantial improvement over previously known approaches. The present invention includes apparatus, and corresponding systems and methods, for secondary imaging during the operation of a CBBCT imaging system, including stationary scan imaging.

Accordingly, in certain embodiments and aspects, the invention includes a process and method of disposing a patient in operative relation to a CBBCT system, orienting the imaging apparatus of the CBBCT system in a desired relationship with respect to a breast of the patient such that a beam of x-rays produced by the CBBCT system has a longitudinal axis that traverses generally normal to a desired cross-section of the breast to be imaged, and capturing a stationary (i.e. without a gantry of the CBBCT system in motion) image of the breast using the imaging apparatus of the CBBCT system. The resulting "stationary" image of the breast can then be evaluated directly, and/or the corresponding data of that stationary image can be incorporated and/or hybridized with additional data such as, for example, CBBCT image data captured by the CBBCT system while the gantry is in motion or during a plurality of static imaging events interspersed with gantry motion.

In certain further aspects and embodiments, the invention includes supplemental imaging apparatus that serves to support, stabilize and/or in some embodiments compress, a breast to be imaged or one or more regions of the breast to be imaged. The system thus provides selected images of exceptional detail of the subject breast as a whole, and of specific regions within the breast.

It should be appreciated that the present invention includes both a method of static imaging of the breast in a CBBCT without supplementary equipment, and such imaging along with the use of supplementary stabilization and/or compression apparatus.

The following description is provided to enable any person skilled in the art to make and use the disclosed inventions and sets forth the best modes presently contemplated by the inventors of carrying out their inventions. In the following description, for purposes of explanation, numerous specific details are set forth in order to provide a thorough understanding of the present invention. It will be apparent to one skilled in the art, however, that the present invention may be practiced without these specific details. In other instances, well-known structures and devices are shown in block diagram form in order to avoid unnecessarily obscuring the substance disclosed. These and other advantages and features of the invention will be more readily understood in relation to the following detailed description of the invention, which is provided in conjunction with the accompanying drawings.

It should be noted that, while the various figures show respective aspects of the invention, no one figure is intended to show the entire invention. Rather, the figures together illustrate the invention in its various aspects and principles. As such, it should not be presumed that any particular figure is exclusively related to a discrete aspect or species of the invention. To the contrary, one of skill in the art will appreciate that the figures taken together reflect various embodiments exemplifying the invention.

Correspondingly, referenced throughout the specification to "one embodiment" or "an embodiment" means that a particular feature, structure, or characteristic described in connection with the embodiment is included in at least one embodiment of the present invention. Thus, the appearance of the phrases "in one embodiment" or "in an embodiment" in various places throughout the specification are not necessarily all referring to the same embodiment. Furthermore, the particular features, structures, or characteristics may be combined in any suitable manner in one or more embodiments.

DETAILED DESCRIPTION

The following description is provided to enable any person skilled in the art to make and use the disclosed inventions and sets forth the best modes presently contemplated by the inventors for carrying out their inventions. In the following description, for purposes of explanation, numerous specific details are set forth in order to provide a thorough understanding of the present invention. It will be apparent, however, to one skilled in the art that the present invention may be practiced without these specific details.

It should be noted that while any of the embodiments described for exemplary purposes below will identify specific elements and combinations of elements, these examples are not intended to be determinative. Rather, discrete elements will, in appropriate circumstances, be combined into integral elements and/or assemblies. Further, the present disclosure of aspects and features of particular elements described herewith as integral, should be understood to convey also the disclosure of individual elements and assemblies providing the same characteristics and/or functionality.

Figure 1:
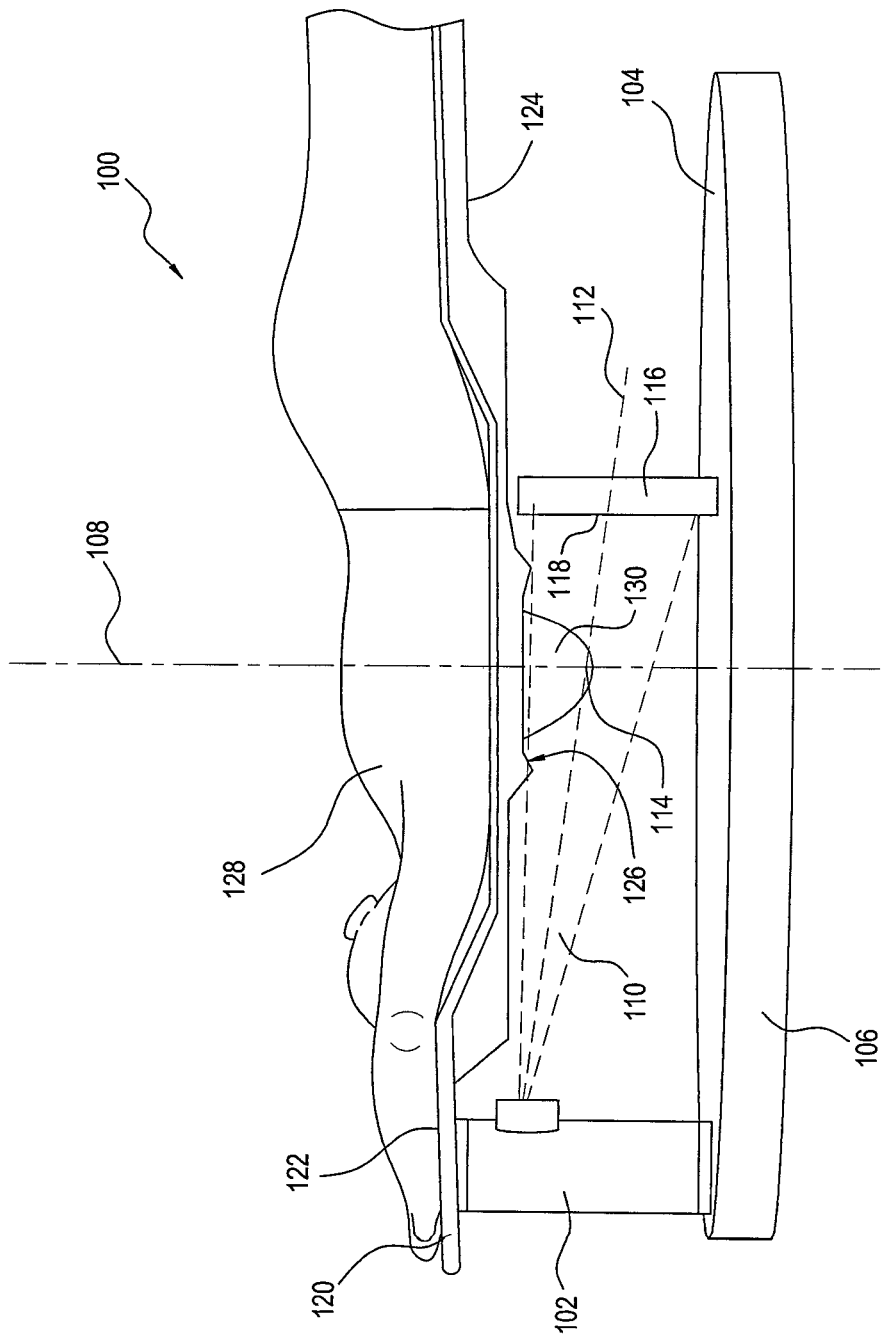
FIG. 1 shows in cutaway perspective view, a portion of an exemplary CBBCT imaging system.

FIG. 1 shows, in cutaway perspective view, a portion of an exemplary CBBCT imaging system 100. The system 100 includes an x-ray source 102. The x-ray source 102 is mounted on an upper surface 104 of a rotating gantry 106. The rotating gantry 106 is supported by a bearing, and arranged for rotation about an axis of rotation 108.

The x-ray source 102 is configured to emit a beam of x-rays 110. The beam of x-rays 110 defines a beam longitudinal axis 112 that, in the illustrated embodiment, intersects (at 114) the axis of rotation 108.

In certain embodiments of the invention, beam 110 is configured as a cone beam. In certain configurations, a cross-section of the beam 110 taken transverse to the longitudinal axis 112 defines a disk of substantially uniform x-ray intensity with a substantially circular perimeter.

In other configurations within the scope of the invention, a cross-section of the beam 110 taken transverse to the longitudinal axis 112 defines a region of substantially uniform x-ray intensity with a substantially circular perimeter save for a portion of the disc outwardly of a chord of said circular perimeter. As will be appreciated on consideration of the further disclosure below, in certain embodiments, the chord will be disposed in generally parallel spaced relation to a lower surface of a patient table.

Accordingly, in certain configurations, a cross-section of the beam 110 taken transverse to the longitudinal axis 112 defines a truncated disk of substantially uniform x-ray intensity with a substantially truncated circular perimeter (i.e., a perimeter that is circular except for a horizontal chord of the circle at its upper periphery). This configuration optimizes imaging of the breast while minimizing irradiation of chest wall tissue above the breast. It is implemented, in certain embodiments, by the placement of an x-ray-opaque collimating plate across a portion of an otherwise circular cross-section beam generated by the x-ray source.

In still further configurations within the scope of the invention, a cross-section of the beam 110 taken transverse to the longitudinal axis 112 defines a region of substantially uniform x-ray intensity with a polygonal perimeter, where the polygonal perimeter will, in respective embodiments and configurations, include any of a triangular perimeter, a rectangular perimeter, a pentagonal perimeter, hexagonal perimeter, a perimeter of any higher geometric shape, or a perimeter having any arbitrary curve or combination of line segments and curves according to the demands of a particular application. Moreover, it will be appreciated that any of the cross-sectional configurations described above may define a beam having a nonuniform intensity including, without limitation an intensity that falls to zero in a region, or certain regions, of the cross-section.

An x-ray detector 116 is also mounted on the upper surface 104 of the rotating gantry 106. In one exemplary embodiment, the x-ray detector 116 includes a flat panel detector having a generally planar receiving surface 118. Receiving surface 118 is disposed generally transverse to longitudinal axis 112 and on the opposite side of axis of rotation 108 from the x-ray source 102. It will be appreciated by one of skill in the art that the configuration described is merely exemplary of many possible arrangements in which the x-ray source, the x-ray detector, and any other component of the system, maybe supported from above, from a side, or in any other way appropriate to achieving the desired function, and that the shape and configuration of the gantry, and of the x-ray detector, will likewise assume any useful form in respective embodiments of the invention.

Rotation of the gantry 106 about axis of rotation 108 during operation of the imaging system 100 will result in the receiving surface 118 following a transit path about axis of rotation 108. In a typical configuration, the transit path will include at least a portion of a circle disposed transverse to, and centered at, axis of rotation 108. It should be noted, however, that other transit paths are considered to be within the scope of the invention, and to be disclosed herewith.

In certain embodiments of the invention, one or both of the x-ray source 102 and the x-ray detector 116 are arranged so that their respective positions on the upper surface 104 of gantry 106 are adjustable. For example, the x-ray source 102 and the x-ray detector 116 may be adjustable in a radial direction with respect to axis of rotation 108, in a circumferential direction with respect to axis of rotation 108, in a direction towards or away from gantry surface 104, or in any other manner deemed beneficial by the designer or user of a particular apparatus embodying the invention.

A patient table 120 includes an upper surface 122 and a lower surface 124. An aperture 126 communicates between the upper surface 122 and lower surface 124 of the table. The upper surface 122 is arranged to support a patient 128, typically with the patient lying prone on surface 122, as illustrated. In this arrangement, a breast 130 of the patient is disposed pendant from the patient's chest wall downwardly through aperture 126.

In operation, the gantry rotates about axis of rotation 108, carrying x-ray source 102 and x-ray detector 116 in transit in a path around the patient's breast. During this transit, x-ray image data is captured by operation of the x-ray detector 116 in conjunction with corresponding interface electronics and computer systems. The x-ray image data corresponds to a plurality of x-ray images taken at respective angular locations about axis of rotation 108. Taken together, the x-ray image data, or a subset of the same, is processed to provide information about the internal state of the breast.

Figure 2:
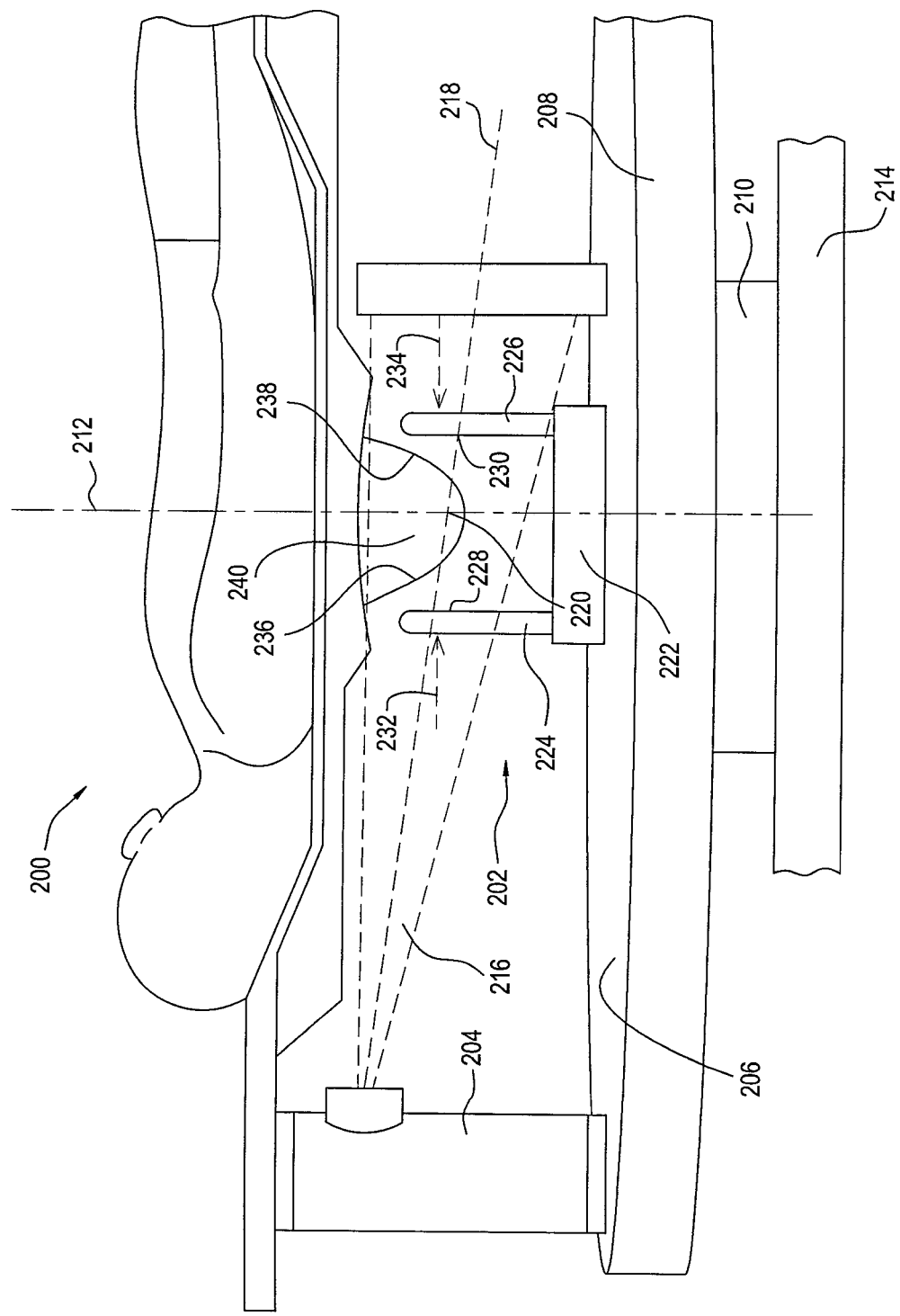
FIG. 2 shows, in schematic side elevation, a portion of an exemplary CBBCT imaging system including a stationary imaging subsystem prepared according to principles of the invention.

FIG. 2 shows, in schematic side elevation, a portion of an exemplary CBBCT imaging system 200, including a stationary imaging subsystem 202 prepared according to principles of the invention.

Like system 100 described above, system 200 includes an x-ray source 204. The x-ray source 204 is mounted on an upper surface 206 of a rotating gantry 208. The rotating gantry 208 is supported by a bearing 210, and arranged for rotation about an axis of rotation 212. The bearing 210 is, in turn, supported by a structural member 214 of the imaging system 200 or, alternately, by a floor.

The x-ray source 204 is configured to emit a beam of x-rays 216. The beam of x-rays 216 defines a beam longitudinal axis 218 that, in the illustrated embodiment, intersects (at 220) with the axis of rotation 212.

In the exemplary embodiment presented here, stationary imaging subsystem 202 has a base portion 222 including a translation apparatus, a first effector panel 224 and a second effector panel 226. First effector panel 224 has a first breast contact surface region 228. Second effector panel 226 has a second breast contact surface region 230.

In certain embodiments of the invention, the translation apparatus includes a first translation portion and a second translation portion. The first translation portion is operatively coupled between the base portion 222 and the first effector panel 224. The second translation portion is operatively coupled between the base portion 222 and the second effector panel 226.

In certain embodiments, the respective first and second translation portions operate to translate the first effector panel 224 and second effector panel 226 in respective first 232 and second 234 directions towards one another relative to base 222, in response to respective first and second input signals. In other embodiments of the invention, a common input signal will be effective to activate both the first and second translation portions.

As first 224 and second 226 effector panels move towards one another, respective breast contact surface regions 228, 230 are urged into contact with respective surface regions 236, 238 of a patient breast 240. Appropriate further displacement of the effector panels 224, 226 serves to provide compression, support and stabilization of the breast 240 for imaging, as discussed more comprehensively below.

Figure 3:
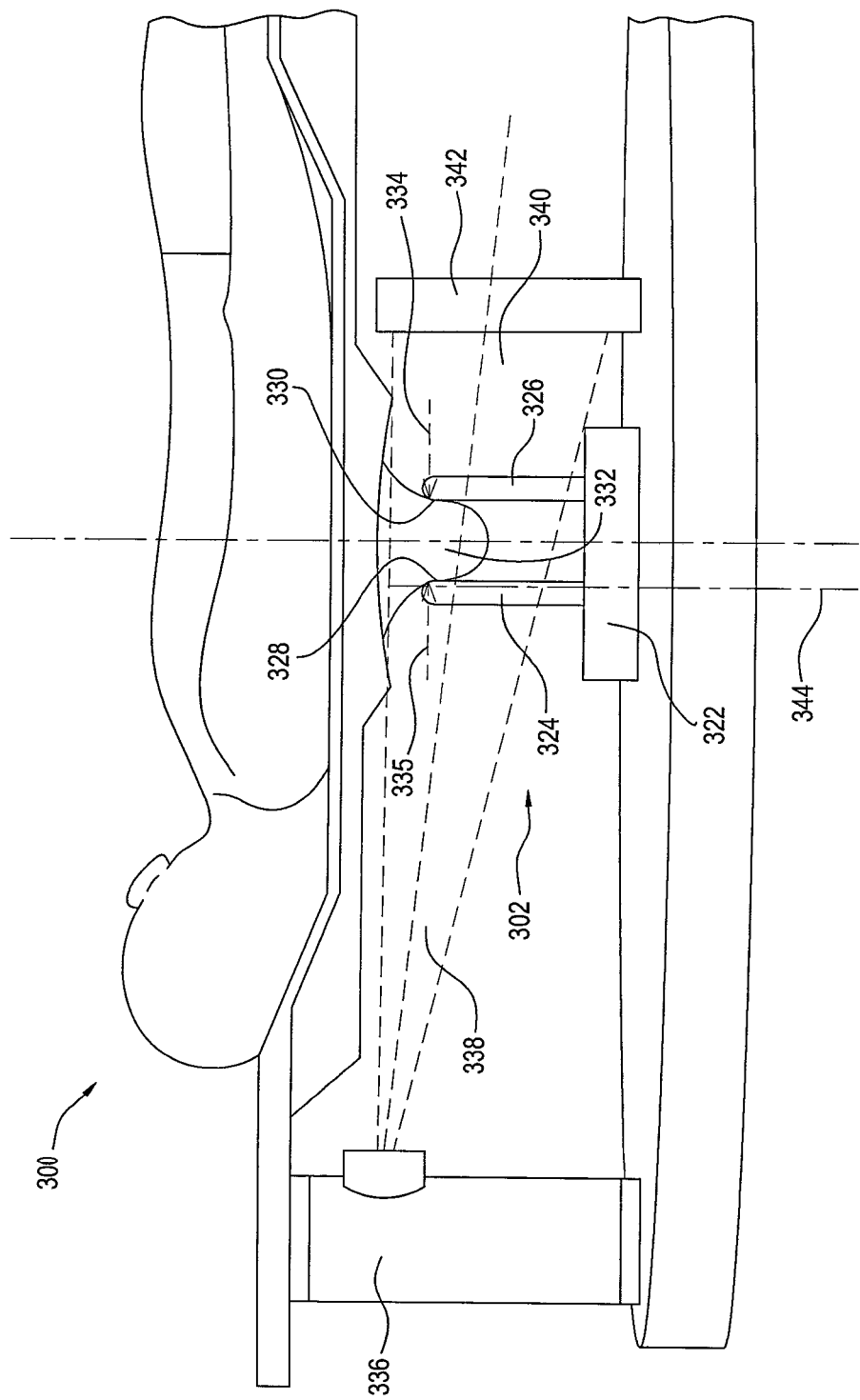
FIG. 3 shows, in schematic side elevation, a portion of an exemplary CBBCT imaging system including a stationary imaging subsystem prepared according to principles of the invention.

FIG. 3 shows, in schematic cutaway side elevation, a portion of an exemplary CBBCT imaging system 300, including a stationary imaging subsystem 302 prepared according to principles of the invention.

Like system 200 described above, system 300 includes stationary imaging subsystem 302 with a base portion 322 including a translation apparatus, a first effector panel 324 with a first breast contact surface region 328 and a second effector panel 326 with a second breast contact surface region 330.

In the illustrated configuration, breast 332 is compressed in directions 334, 335 and stabilized by the inward urging of the effector panels 324, 326. Thereafter x-ray source 336 produces a beam of x-rays 338 that passes through first effector panel 324, breast 332, and second effector panel 326. The passage of the x-ray beam 338 through breast 332 serves to produce a modulated region 340 of the x-ray beam. The modulated x-ray beam is received at x-ray detector 342. X-ray detector 342 in turn produces image data for display as a static image, or for further processing including, in some cases, hybridization with tomographic image data otherwise produced by the CBBCT system 300.

The practitioner of ordinary skill in the art will appreciate that the form, configuration and materials of the effector panels will be selected to provide optimal compression and support of the breast. In addition, and as will be further discussed below, in certain embodiments of the invention the effector panel will be configured or selected to compress a limited region of the breast. Also, in certain embodiments of the invention, compression directions 334, 335 will be selected to achieve optimal imaging without requiring the degree of compression (and accordingly pain) experienced by a patient in conventional mammography.

In certain aspects and embodiments of the invention, the effector panel (e.g., 324) will be selected to flex along a vertical axis 344 so as to conform more effectively to the breast 332, and so as to distribute force over the breast surface, thereby increasing patient comfort in some cases.

In certain aspects and embodiments of the invention, the degree to which the breast is compressed along directions 334, 335 will be selected according to the requirements of a particular imaging procedure or protocol, the characteristics of the breast (including, for example and without limitation tissue density), the suspected presence of a particular pathology, or any other diagnostic or procedural consideration considered significant by the operating medical or technical personnel.

In light of the foregoing, in certain embodiments and applications of the invention, a subject breast will be compressed along directions 334, 335 by at least about 2%, by at least about 5%, by at least about 10%, by at least about 20%, by at least about 30%, by at least about 40%, or by at least about 50%. In other applications any desirable, optimized or properly tolerated degree of compression will be applied.

Figure 4:
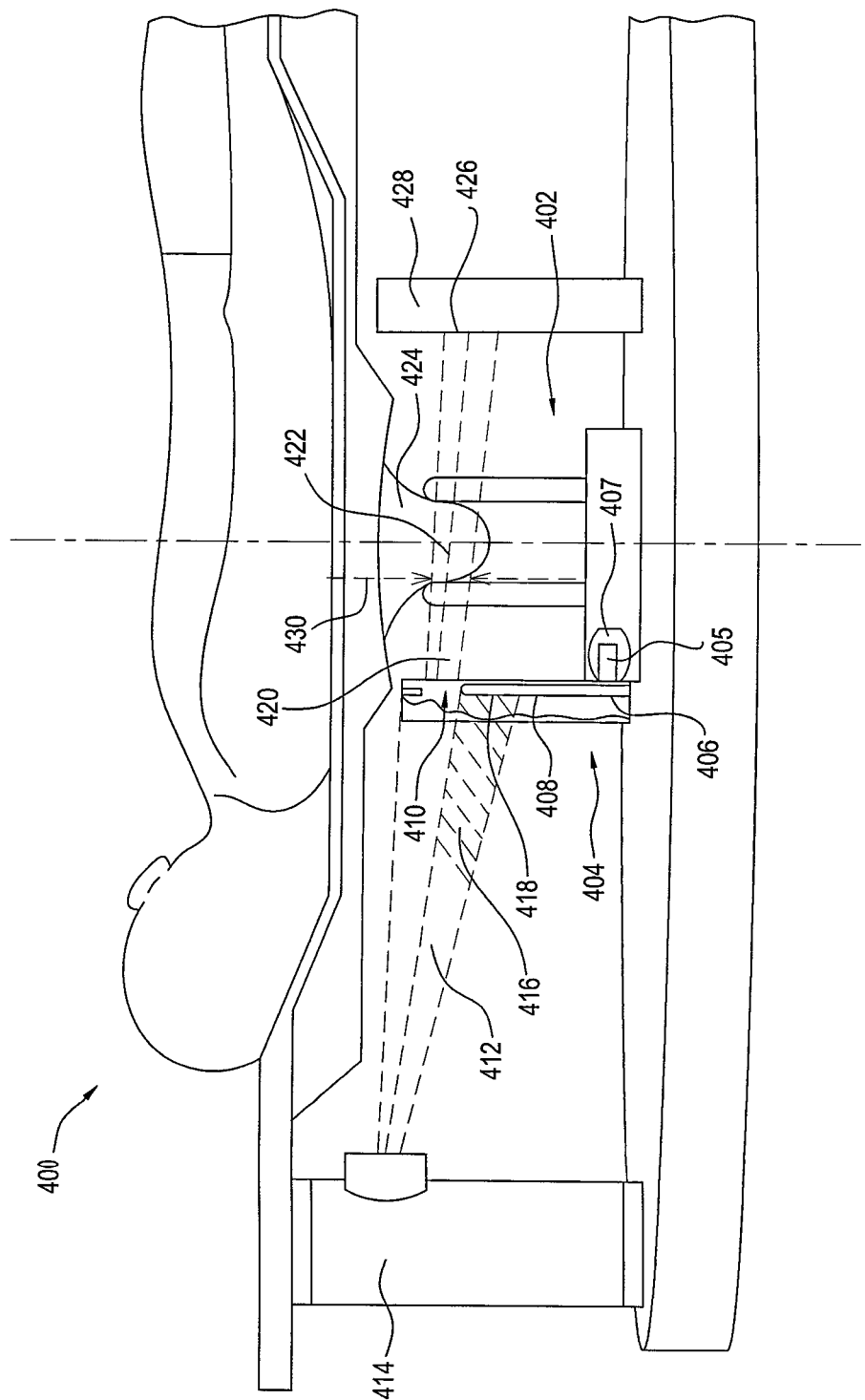
FIG. 4 shows, in schematic side elevation, a portion of an exemplary CBBCT imaging system including a stationary imaging subsystem prepared according to principles of the invention.

FIG. 4 shows, in schematic cutaway side elevation, a portion of a further exemplary CBBCT imaging system 400 (similar in many respects to system 300), and including a stationary imaging subsystem 402. As shown, system 400 includes a collimator subsystem 404.

The collimator subsystem 404 includes a collimator device 406. The collimator device 406 includes a substantially x-ray opaque portion 408, and an aperture (or a relatively x-ray transparent portion, i.e. a window, or both) 410 within the relatively opaque portion 408. Note here that the relative terms relatively opaque and relatively transparent represent a comparison between the respective elements 408 and 410.

In the illustrated embodiment, the collimator subsystem 404 includes a collimator coupler 405. The collimator coupler 405 is adapted to be received within and coupled to a collimator receiver 407 of the stationary scan subsystem 402. Accordingly, the collimator coupler 405 and collimator receiver 407 combination serves to removably couple the collimator subsystem 404 to the stationary scan subsystem 402 for substantial support and positioning.

In the illustrated embodiment, the collimator subsystem 404 is disposed within a beam of x-rays 412 produced by an x-ray source 414. In operation, the collimator subsystem 404 is arranged such that a first portion 416 of the beam of x-rays impinges on, and accordingly is blocked by, a corresponding portion 418 of the x-ray opaque portion 408.

A second portion 420 of x-ray beam 412 passes through the aperture and/or window 410 and thus impinges on a limited region 422 of a breast 424 being imaged. The second portion 420 of x-ray beam 412 is modulated by its passage through the limited breast region 422 and this modulated beam is detected at a corresponding region 426 of an x-ray imager 428.

The dimensions 430 of the limited breast region 422 exposed to the second portion 420 of the x-ray beam is determined by the corresponding dimensions of the aperture or window 410. Accordingly, the presence of the collimator subsystem 404 allows for selective imaging of a limited breast region 422, thus providing additional detail/resolution as to that region, while avoiding undue x-ray exposure of the balance of the breast 424.

In certain embodiments and aspects of the invention, CBBCT system 400 including a stationary imaging subsystem 402 and a collimator subsystem 404 will include a collimator subsystem having a reconfigurable aperture or window 410. Such a reconfigurable collimator subsystem will, in certain aspects of the invention, permit the placement and configuration of the aperture/window at substantially any operative location within the collimator subsystem so as to allow the selective x-ray illumination of any desired limited breast region 422, while effectively protecting the balance of the breast from unnecessary x-ray exposure.

In certain embodiments of the invention, the placement and configuration of the aperture/window 410 will be effected by the insertion of a preconfigured collimator device 406 into a receiver of the collimator subsystem 404, where the preconfigured collimator device 406 includes an aperture/window 410 of a particular desired dimension and/or location within the collimator device 406. When a different region of a breast is to be illuminated, the collimator device 406 is removed and a differently configured collimator device 46 is installed.

FIGS. 5A-5F shows a variety of collimator bodies and configurations including respective aperture/window arrangements each of which will be installed in a single collimator subsystem 404 to achieve a desired respective configuration of a beam region (as shown, e.g., at 420 in FIG. 4).

In the context of the foregoing discussions, FIGS. 5A-5F show, in schematic fashion, a variety of exemplary collimator configurations that fall within the scope of the present invention and are similar to exemplary collimator 406 described above in relation to FIG. 4.

Figure 5A:
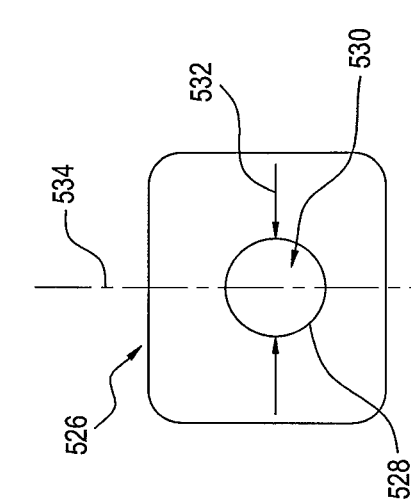
FIG. 5A shows in schematic elevation, an exemplary collimator for a stationary scan subsystem of a CBBCT imaging system prepared according to principles of the invention.
Figure 5B:
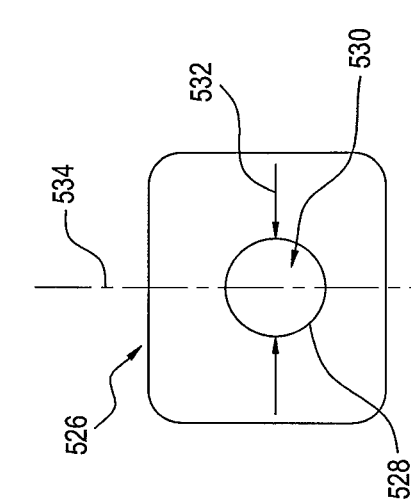
FIG. 5B shows in schematic elevation, a further exemplary collimator for a stationary scan subsystem of a CBBCT imaging system prepared according to principles of the invention.
Figure 5C:
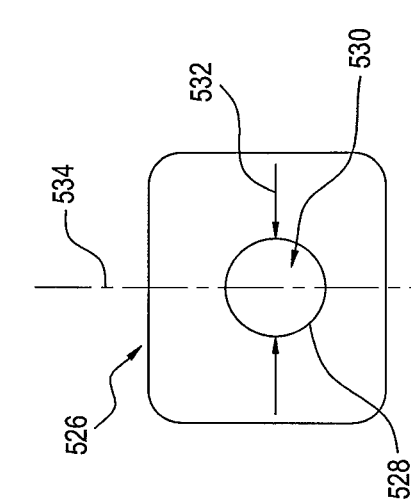
FIG. 5C shows in schematic elevation, another exemplary collimator for a stationary scan subsystem of a CBBCT imaging system prepared according to principles of the invention.

FIGS. 5A-5C show respectively, in schematic elevation, exemplary collimators having a variety of aperture locations and sizes.

Referring first to FIG. 5A, collimator 500 includes a collimator surface region 502. An inner circumferential edge 504 defines a collimator aperture 506 through the collimator. Consistent with the discussion above, the aperture 506 is adapted to receive a patient breast to be imaged therethrough. In the configuration illustrated, the collimator aperture 506 is disposed to the left of a longitudinal centerline 508 of the collimator 500. Accordingly, in typical operation of the CBBCT imaging system, a left breast of the patient will be disposed through the collimator aperture 506 during imaging.

FIG. 5B shows a collimator 512 similar to collimator 500. As with collimator 500, collimator 512 has an inner circumferential edge 514 that defines a collimator aperture 516 through the collimator 512. Like aperture 506, aperture 516 is disposed to the left of a longitudinal centerline 518 of the collimator 512. However, aperture 506 has a diameter 520 that is relatively smaller than the corresponding diameter 522 of aperture 516.

FIG. 5C shows a collimator 526 similar to collimators 500 and 512. As with collimator 500, collimator 526 has an inner circumferential edge 528 that defines a collimator aperture 530 through the collimator 526. Like aperture 506, aperture 530 has a diameter of 532 that is substantially equal to corresponding diameter 522 of aperture 516. However, a centroid of aperture 530 is disposed substantially coincident with centerline 534 of the collimator 526. Accordingly, whereas apertures 506 and 516 are primarily configured for receiving a left breast of the patient for imaging, aperture 530 is well adapted to receiving either a left breast or a right breast.

It will also be appreciated by one of skill in the art that, where appropriate perimeter configurations and coupling features are provided, symmetries of the illustrated panels will be used in respective embodiments of the invention to image, for example, either a left breast or a right breast by symmetric rotation of collimator 500 or 512 about centerlines 508 and 518 respectively.

Likewise, rotation of the panels about an axis transverse to the centerlines can be used to locate the illustrated apertures relatively higher or lower respectively, according to the needs of a taller or shorter patient.

In light of the foregoing discussion, it will be appreciated by the reader that, in certain embodiments of the invention, a plurality of collimators will be provided along with an imaging system, such that the collimator with the appropriate aperture will be selected according to the height, weight, breast size and other parameters of the patient.

In another aspect embodiment of the invention, individual reusable collimators will be purchased so as to be available where required. In still other embodiments of the invention, disposable collimators will be employed for single use with a respective patient, and thereafter discarded.

Figure 5D:
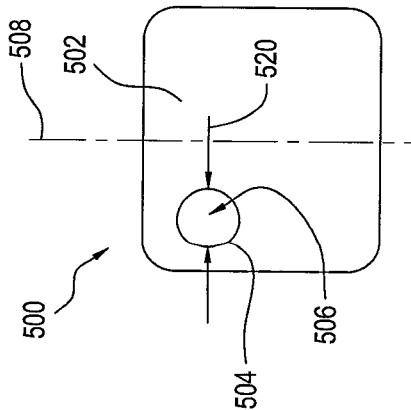
FIG. 5D shows in schematic elevation, an exemplary shielding collimator, including an adjustable iris mechanism, for a stationary scan subsystem of a CBBCT imaging system prepared according to principles of the invention.
Figure 5E:
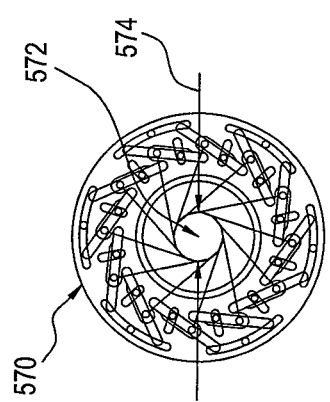
FIG. 5E shows in schematic elevation, an exemplary adjustable iris mechanism, for a stationary scan subsystem of a CBBCT imaging system prepared according to principles of the invention.
Figure 5F:
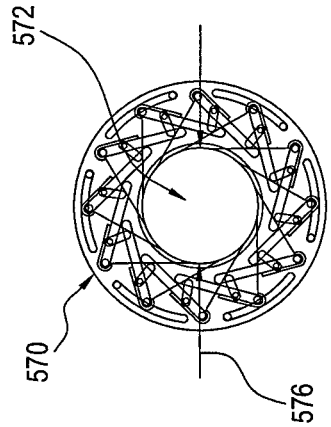
FIG. 5F shows in schematic elevation, a further exemplary adjustable iris mechanism, for a stationary scan subsystem of a CBBCT imaging system prepared according to principles of the invention.

FIGS. 5D-5F show schematic representations of a further collimator 550 prepared according to principles of the invention. Collimator 550 is shown in cutaway view, and illustrates an adjustment mechanism 552 included in collimator 550.

In the exemplary embodiment illustrated, adjustment mechanism 552 includes a mechanical iris mechanism 554. The adjustable iris mechanism 554 includes a plurality of leaf elements, e.g., 556, 558 respectively coupled to corresponding operative links 560, 562. One of skill in the art will recognize the adjustable iris mechanism 554 as similar in form and function to iris mechanisms employed in photographic cameras. Accordingly, by operation of the operative links 560, 562, the leaf elements 556, 558 will be urged to pivot so as to adjust a diameter of an aperture 564 to a preferred value according to the requirements for imaging a particular patient breast.

By way of further illustration, in FIG. 5E exemplary iris mechanism 570 is adjusted and configured to present an aperture 572 having a relatively small diameter 574. In FIG. 5F, exemplary iris mechanism 570 is adjusted and configured to present the same aperture 572 with a relatively large diameter 576.

In certain embodiments the shielding collimator 550 of FIG. 5D will be manually adjustable by direct manipulation of the leaf elements (leaves). In other embodiments, an adjustment mechanism will be provided to reconfigure the leaf elements. In still other embodiments of the invention, an automatic adjustment mechanism will provide automatic adjustment of the leaf elements and therefore of the aperture of the collimator.

In certain embodiments of the invention, the automatic adjustment mechanism for the leaf elements will include a linear actuator. In such an embodiment and throughout the present application, a linear actuator will include, by way of example, any of a wide variety of actuators. For example, in certain embodiments, the extension mechanism will include one or more of a rack and pinion apparatus; an Acme screw and Acme nut; a ballscrew apparatus; a linear stepping motor; a transverse complementary ramps; a pneumatic cylinder; a pneumatic bladder; a pneumatic bellows; a hydraulic cylinder; a hydraulic bladder; a hydraulic bellows; a scissors linkage mechanism, including, for example, a scissors linkage mechanism linkage operated by a lead screw, a cylinder, or any of the other actuators discussed herewith, or any other appropriate actuator; a sarrus linkage mechanism; a thermoelectric actuator; a shape memory alloy actuator; a cable and pulley arrangement; a compressive spring; a tension spring; a torsion spring; an assembly of leaf springs; a spring including a plurality of Belleville washers; or any other linear actuator element currently known, or that becomes known in the art, that is suited to the requirements of a particular application and to providing the requisite extension function.

Thus for example, in certain embodiments of the invention, the linear actuator will include one or more of an electrical solenoid, a pneumatic cylinder, a hydraulic cylinder, a pneumatic bladder, a hydraulic bladder, a linear electric motor, linear stepping motor, a rotary actuator along with: an Acme screw and nut, a lead screw, a ballscrew, a cable, a pulley, a timing belt, a timing pulley, an appropriately sized worm gear reducer, a rack and pinion assembly, a rack and worm gear assembly; a piezoelectric actuator, a piezoelectric actuator combined with a ratchet and pawl driver, a spring loaded actuator, an actuator including a shape memory alloy, as well as any of a wide variety of manual actuators such as, for example, a handcrank and/or a ratchet lever and any other appropriately functioning actuator component that is known or becomes known in the art.

Figure 6:
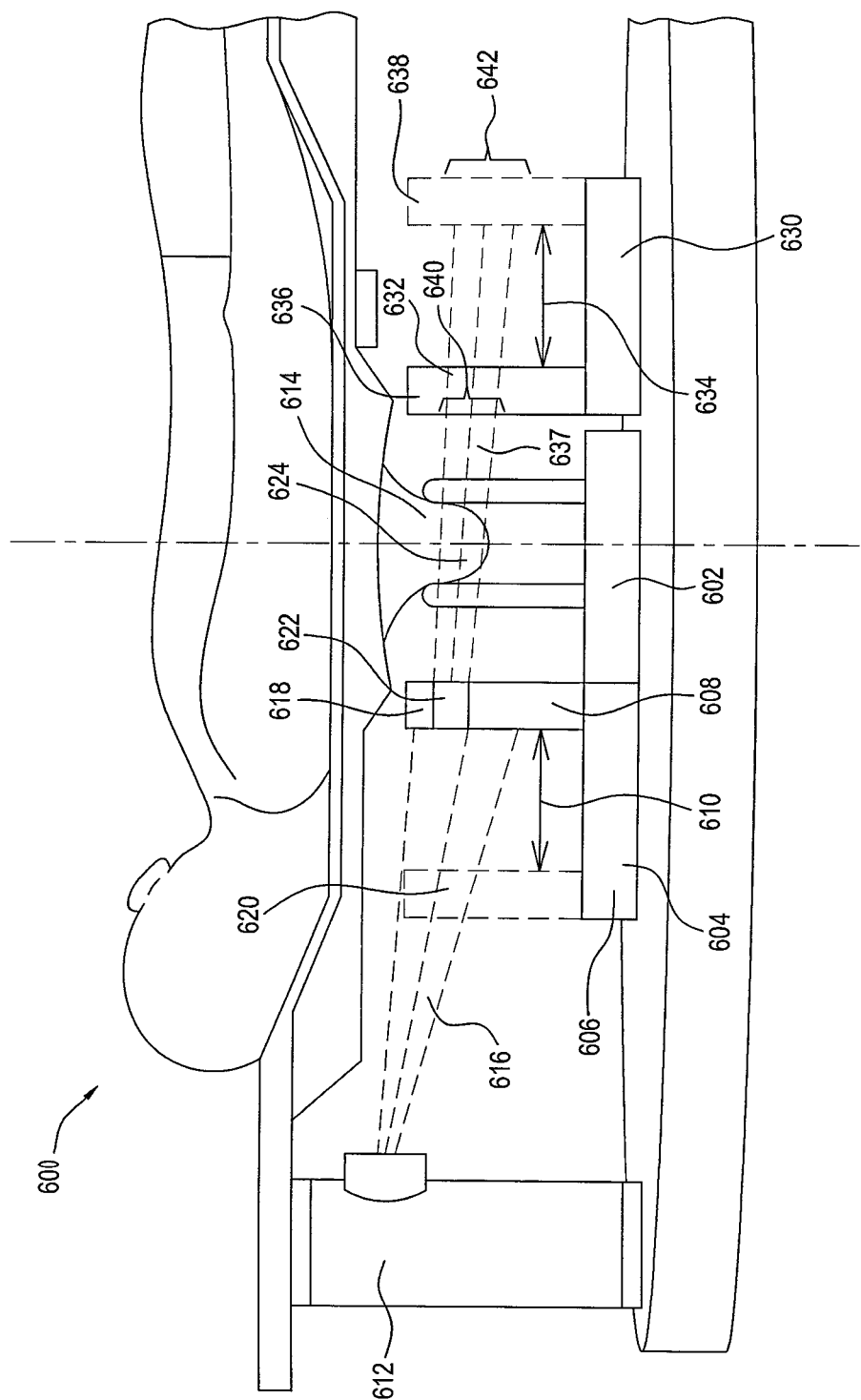
FIG. 6 shows, in schematic side elevation, a portion of a further exemplary CBBCT imaging system including a stationary imaging subsystem prepared according to principles of the invention.

FIG. 6 shows, in schematic cutaway side elevation, a portion of a further exemplary CBBCT imaging system 600 (similar in many respects to system 400), and including a stationary imaging subsystem 602 and a collimator subsystem 604.

In the illustrated exemplary system 600, the collimator subsystem 604 includes a collimator translation portion 606 and a collimator device 608. The collimator translation portion 606 is coupled to, and supports, the collimator device 608. The collimator translation portion 606 is operable to adjust 610 a position of the collimator device 608 with respect to an x-ray source 612 and a breast 614 being imaged, and thus with respect to a beam of x-rays 616 produced by the x-ray source 612.

It will be apparent to one of skill in the art that adjusting the position of the collimator device 608 between a first position 618 and a second position 620 will, for a particular configuration of an aperture/window results in the illumination of a correspondingly different region 624 of breast 614.

In certain embodiments of the invention it will be desirable to have a plurality of collimator devices, as exemplified by collimator device 608.

System 600 also includes an imager translation portion 630. The imager translation portion 630 is coupled to, and supports, an imager 632. The imager translation portion 630 is operable to adjust 634 a position of the imager 632 with respect to an x-ray source 612 and a breast 614 being imaged, and thus with respect to a portion 637 of x-ray beam 616 produced by the x-ray source 612.

It will be apparent to one of skill in the art that adjusting the position of the imager 632 between a first position 636 and a second position 638 will, for a particular configuration of the collimator device 608 results in the illumination of a correspondingly different region 640, 642 of the imager 632.

Figure 7A:
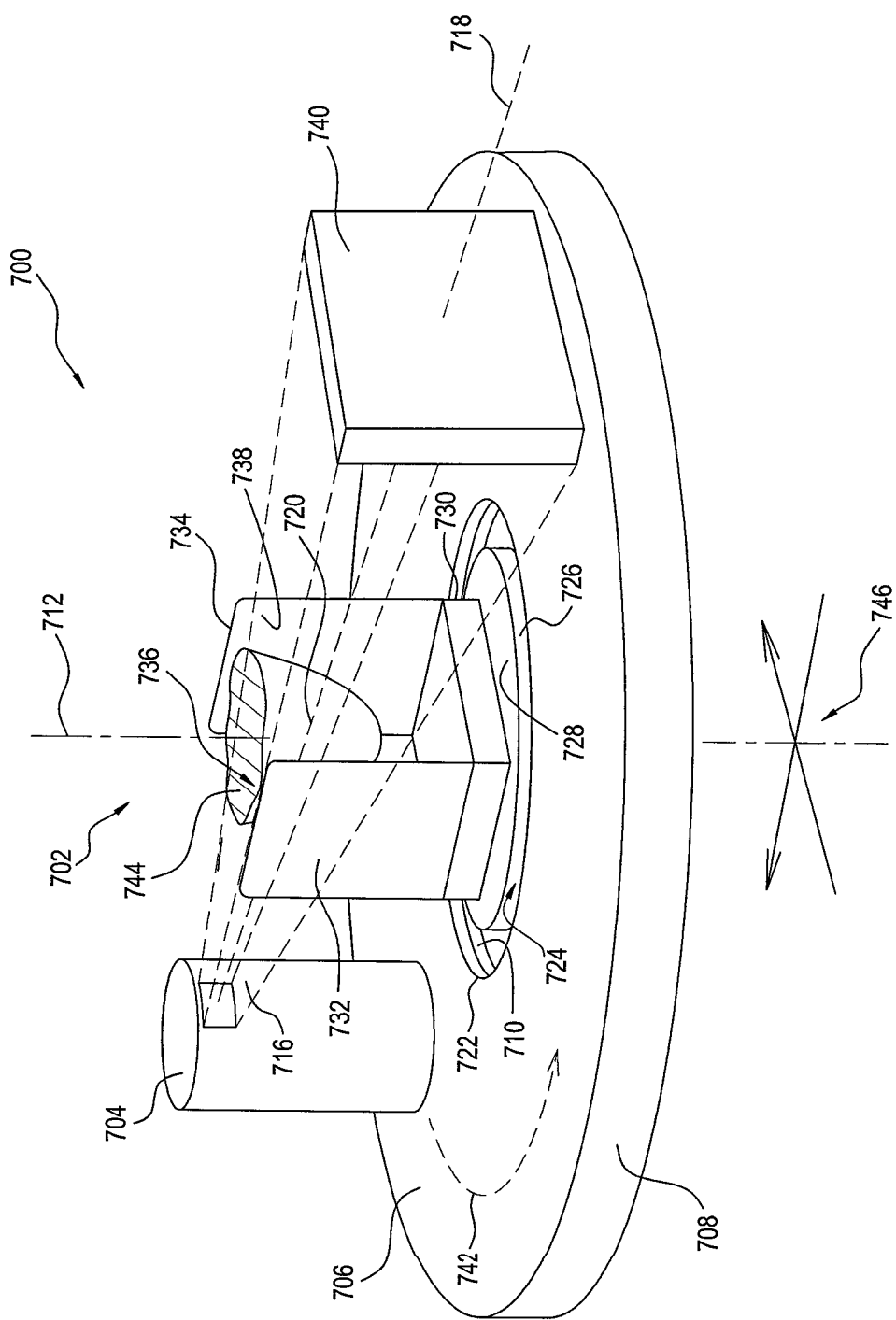
FIG. 7A shows, in schematic side elevation, a portion of an exemplary CBBCT imaging system including a stationary imaging subsystem prepared according to principles of the invention.

FIG. 7A shows in schematic perspective view, a CBBCT imaging system 700, including a stationary imaging subsystem 702, prepared according to principles of the invention.

Similar to system 200, and others, described above, system 700 includes an x-ray source 704. The x-ray source 704 is mounted on an upper surface 706 of a rotating gantry 708. The rotating gantry 708 is supported by a bearing 710, and arranged for rotation about an axis of rotation 712. The bearing 710 is, in turn, supported by a structural member of the imaging system 700 or, alternately, by a floor.

The x-ray source 704 is configured to emit a beam of x-rays 716. The beam of x-rays 716 defines a beam longitudinal axis 718 that, in the illustrated embodiment, intersects (at 720) the axis of rotation 712.

In the illustrated embodiment, the upper surface 706 of the rotating gantry 708 includes an internal circumferential edge 722. The internal circumferential edge 722 defines an aperture 724 through the upper surface 706 of the gantry 708.

In certain embodiments of the invention, the rotating gantry 708 includes a slip-ring for communicating power and/or electronic signals and/or optical signals on and off of the gantry. In certain embodiments of the invention, the slip ring includes an aperture disposed generally coaxially with the aperture 724 of the gantry.

In other embodiments of the invention, information and control signals are communicated on and off of the gantry through wireless modulated electromagnetic radiation signals including, without limitation, any of radiofrequency microwave and/or optical frequency electromagnetic radiation.

In the illustrated embodiment, rotary apparatus 726 is disposed within aperture 724. In certain aspects and embodiments of the invention, the rotary apparatus 726 is supported by a structural member of the imaging system 700 or, alternately, by the floor.

As illustrated, the exemplary rotary apparatus 726 has an upper surface 728. The rotary apparatus 726 permits rotation about axis of rotation 712 of the upper surface 728 with respect to the floor and, optionally, with respect to the longitudinal axis 718 of the x-ray beam 716 (as well as the gantry 708 and the x-ray source 704).

Accordingly, in certain embodiments of the invention, upper surface 728 of the rotary apparatus 726 will rotate independently of upper surface 706 of the gantry 708. In further embodiments and aspects of the invention, upper surface 728 of the rotary apparatus 726 will remain stationary with respect to the room while the upper surface 706 of the gantry 708 rotates with respect to the room. In still other embodiments of the invention, rotation of the upper surface 728 of rotary apparatus 726 will be synchronized to rotation of the upper surface 706 of the gantry 708, and in still other embodiments and aspects of the invention, upper surface 728 of the rotary apparatus 726 will counter rotate with respect to the upper surface 706 of the gantry 708.

In certain embodiments of the invention, differential rotation and/or co-rotation of the upper surface 728 with respect to upper surface 706 will be controlled using, for example, a rotary drive including elements such as, for example, an electric motor such as, e.g., a squirrel cage motor, a pancake motor or a capacitor start motor, a stepper motor, hydraulic motor, pneumatic motor, a spring motor, a piezoelectric motor, a gear train including, for example, one or more pinion gears or one or more worm gears, a ratchet drive mechanism, a chain and sprocket mechanism, a belt and sheave mechanism, and/or a timing belt and timing pulley mechanism, including any combination of the foregoing and any other appropriate device and/or mechanism known or that becomes available to one of skill in the art.

In certain embodiments of the invention, differential rotation and/or co-rotation of the upper surface 728 with respect to upper surface 706 will be controlled using output signals from a system digital computer and/or a system digital controller. In other aspects and embodiments of the invention, differential rotation and/or co-rotation of the upper surface 728 with respect to upper surface 706 will be controlled using dedicated hardware such as, for example, embedded specialized motion control hardware including, for example, motion control integrated circuits, power amplifiers, feedback elements including, for example, limit switches, Hall effect sensors, optical sensors, resolvers, optical encoders, resistive encoders, and the like, any of which will be employed in implementing generalized motion control and/or phase locked loop control.

In still other embodiments and aspects of the invention, differential rotation and/or co-rotation of the upper surface 728 with respect to upper surface 706 will be controlled using a mechanical coupling between the upper surface 728 and the upper surface 706 where, in certain embodiments, the mechanical coupling will be controllable subject to manual and/or automatic configuration and control and where, in certain embodiments, the mechanical coupling includes one or more of a solenoid controlled latch, a rotary motor control latch, a pneumatically controlled latch, a hydraulically controlled latch, a manually operated latch, a gear train, a drive chain, a belt or timing belt, a mechanical, hydraulic or electrical clutch, any of the foregoing in any desirable combination, and any other appropriate mechanism known, or that becomes available, to one of skill in the art.

The stationary imaging subsystem 702 has a base portion 730 including a translation apparatus, a first effector panel 732 and a second effector panel 734. In the exemplary illustration of system 700, base portion 730 is coupled to and supported by upper surface 728 of rotary apparatus 726.

In the illustrated example, first effector panel 732 has a first breast contact surface region 736. Second effector panel 734 has a second breast contact surface region 738.

In certain embodiments of the invention, the translation apparatus includes a first translation portion and a second translation portion. The first translation portion is operatively coupled between the base portion 730 and the first effector panel 732. The second translation portion is operatively coupled between the base portion 730 and the second effector panel 734.

As previously discussed, during CBBCT imaging, gantry 708 is rotated about an axis of rotation 712, carrying x-ray source 704 and imager 740, which are disposed on and supported by upper surface 706, or otherwise coupled to and supported by gantry 708, along a transit path 742 about axis of rotation 712 while a breast 744 being imaged remain stationary with respect to a breast frame of reference 746.

It will be appreciated by one of skill in the art that, depending on the material, arrangement and configuration of the effector panels 732, 734, it will be preferable in some circumstances that the x-ray beam 716 not pass through the effector panels 732, 734 during CBBCT imaging. Rather, the effector panels will be displaced out of the path of the x-ray beam 716 during CBBCT imaging, and only disposed within the path of the x-ray beam 716 during stationary imaging. Accordingly, as illustrated in FIG. 7A, system 700 is configured with stationary imaging subsystem 702 in a storage configuration wherein the breast contacting surfaces 736, 738, are disposed generally parallel to a beam longitudinal axis 718 of x-ray beam 716 and an operational axis of rotation 712 of the stationary scan subsystem is disposed generally transverse to the beam longitudinal axis 718.

In the illustrated storage configuration, x-ray beam 716 passes through breast 744 and onto imager 740 substantially between effector panels 732 and 734 without substantially impinging on either effector panel 732, 734. It will be appreciated by one of skill in the art that, in order to maintain this relationship during CBBCT scanning, rotation apparatus 726 will effect a rotation of upper surface 728 and coordination with the rotation of upper surface 706 throughout the CBBCT scan. One of skill in the art will appreciate, that this coordination may be maintained throughout the length of transit path 742, whether that transit path traverses 3600 through reference frame 746, 180°, or any other angular extent according to the requirements of a particular CBBCT imaging protocol.

It will also be appreciated, in light of the foregoing discussion, that this coordination between the surfaces 728 and 706 will be maintained, in various embodiments, through mechanical, electronic, or other control means.

In contrast, when static imaging is desired, the spatial relationship between upper surfaces 728 and 706 will be decoupled to allow rotation of surface 728 with respect to surface 706. Accordingly, surface 706 will be rotated to arrange longitudinal axis 718 in a desired orientation with respect to breast reference frame 746 so that a desired static image can be captured through the corresponding cross-section of breast 744. Concomitantly, rotary apparatus 726 will rotate surface 728, and accordingly stationary imaging subsystem 702 into a position whereby breast contacting surfaces 736, 738 are disposed generally transverse to longitudinal axis 718 (as then oriented with respect to breast reference frame 746).

This reorientation of upper surface 728 with respect to upper surface 706 serves to adapt stationary imaging subsystem 702 from the storage configuration illustrated in FIG. 7A to an imaging configuration as further discussed below.

Figure 7B:
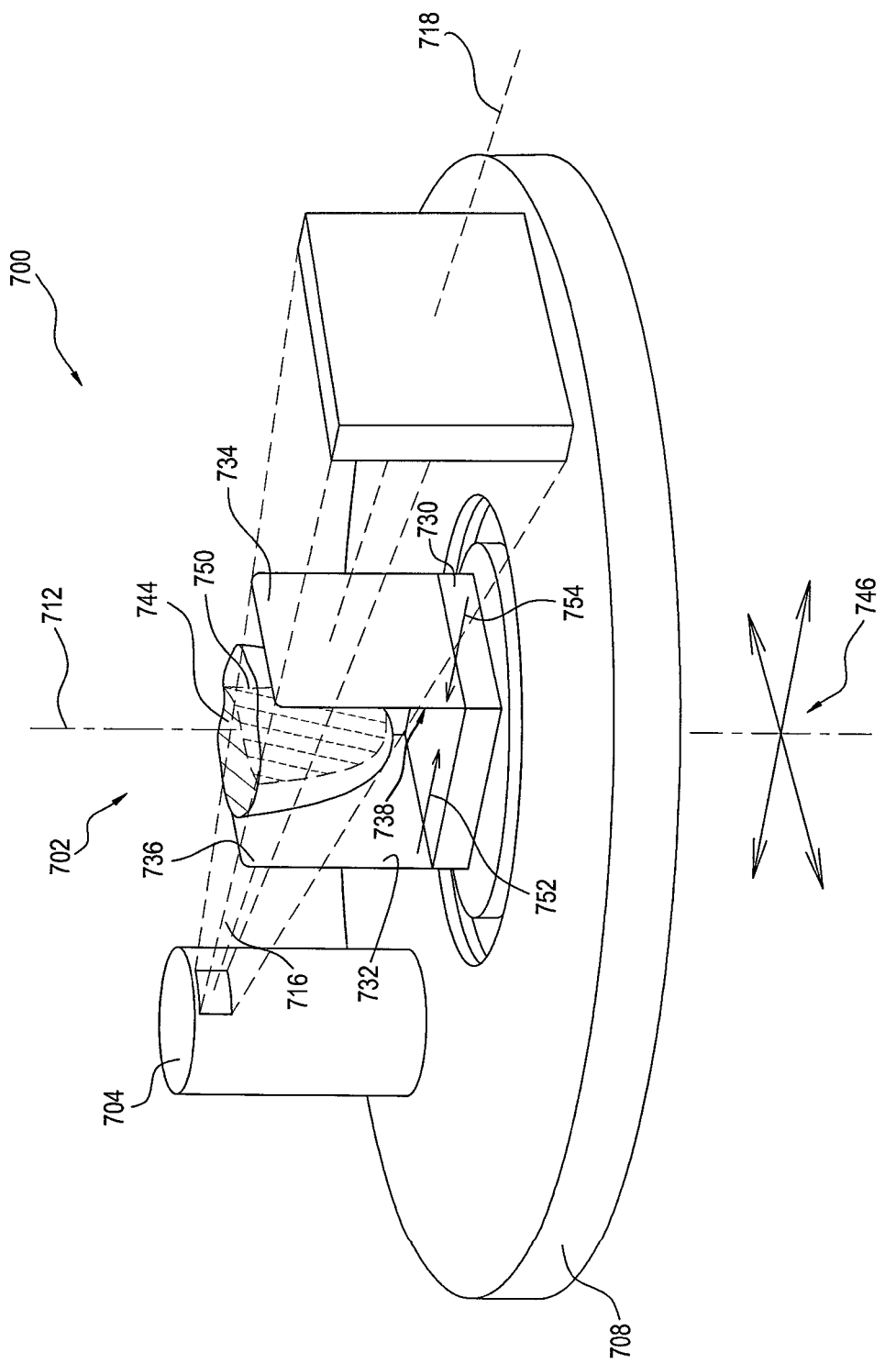
FIG. 7B shows, in schematic side elevation, a portion of an exemplary CBBCT imaging system including a stationary imaging subsystem prepared according to principles of the invention.

FIG. 7B shows in schematic perspective view, further aspects of CBBCT imaging system 700, including stationary imaging subsystem 702, prepared according to principles of the invention and disposed in a stationary imaging configuration.

As illustrated, gantry 708 has been rotated about axis of rotation 712 and arranged with respect to the breast frame of reference 746 so as to dispose x-ray source 704 in a desired relation to the subject breast 744. Accordingly, longitudinal axis 718 of an x-ray beam 716 that will be produced by the x-ray source 704 is disposed generally transverse to (and in a generally normal relation to) a desired cross-section 750 of breast 744 (as identified with respect to breast frame of reference 746).

As also illustrated, stationary scan subsystem 702 has been rotated about axis of rotation 712 and arranged with respect to the breast frame of reference 746 so as to dispose breast contact surface regions 736, 738 in a desired relation to the subject breast 744. Accordingly, longitudinal axis 718 of an x-ray beam 716 that will be produced by the x-ray source 704 is disposed generally transverse to (and in a generally normal relation to) both of breast contact surfaces 736, 738 (as identified with respect to breast frame of reference 746). That is, stationary scan subsystem 702 is disposed in scanning orientation with respect to x-ray source 704 and imager 740.

Thereafter, and generally consistent with the description provided above in relation to FIG. 3, a translation mechanism disposed within base 730 of the stationary scan subsystem 702 is activated to urge effector panels 732, 734 inwardly in respective directions 752, 754 towards the breast 744. The resulting stabilization and, where desirable, compression of the breast 744 is further described below.

Figure 7C:
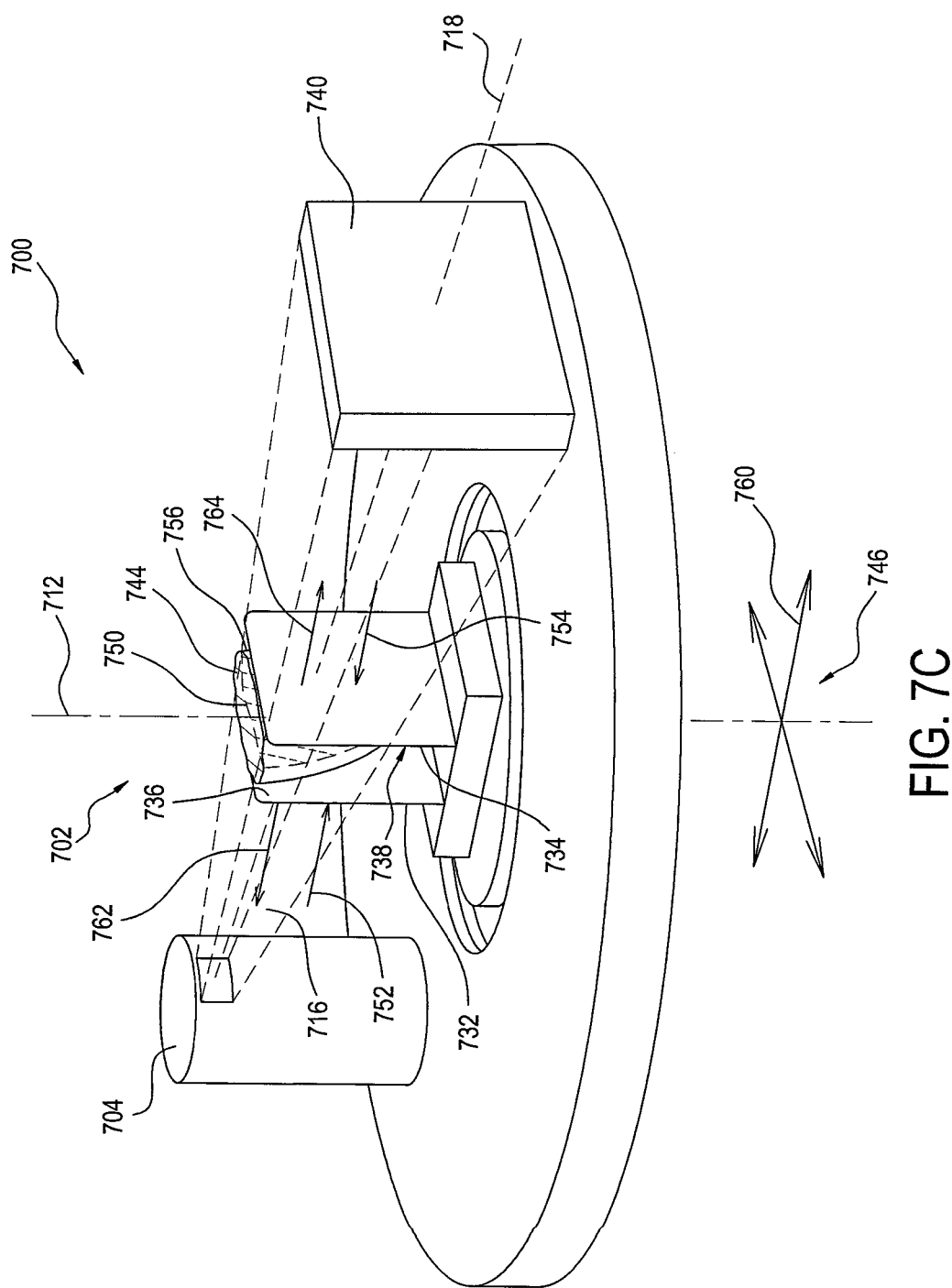
FIG. 7C shows, in schematic side elevation, a portion of an exemplary CBBCT imaging system including a stationary imaging subsystem prepared according to principles of the invention.

FIG. 7C shows in schematic perspective view, further aspects of CBBCT imaging system 700, including stationary imaging subsystem 702, according to principles of the invention.

Consistent with the configuration of system 700 illustrated in FIG. 7B, in FIG. 7C stationary scan subsystem 702 has been rotated about axis of rotation 712 and arranged with respect to the breast frame of reference 746 so as to dispose breast contact surface regions 736, 738 in a desired relation to the subject breast 744. Accordingly, longitudinal axis 718 of an x-ray beam 716 that will be produced by the x-ray source 704 is disposed generally transverse to (and in a generally normal relation to) both of breast contact surfaces 736, 738 (as identified with respect to breast frame of reference 746). That is, stationary scan subsystem 702 is disposed in scanning orientation with respect to x-ray source 704 and imager 740.

As further shown in the exemplary illustration the translation mechanism disposed within base 730 of the stationary scan subsystem 702 has been activated to urge effector panels 732, 734 inwardly in respective directions 752, 754 towards the breast 744. The resulting forces tend to compress the breast 744 generally in parallel with cross-section 750 of the breast, and to stabilize the breast against undesirable motion.

The breast is consequently flattened somewhat to produce, for example, the illustrated cross-section 756 (having a generally flat-oval aspect as taken transverse to axis of rotation 712).

Of course, the reader will appreciate that the image of FIG. 7C may be exaggerated for clarity, as compared to certain actual operations of the method and apparatus described herewith, and that the actual cross-section of the breast will depend on the configuration of a particular breast, on the parameters applied to the system, including the degree of breast compression, the orientation of various elements, etc. Nevertheless, it will be clear to one of ordinary skill in the art that operation of the system described herewith will result in a stabilization and, in some cases reorientation and/or repositioning of the breast tissue that desirably improves the resulting transverse stationary image.

Figure 7D:
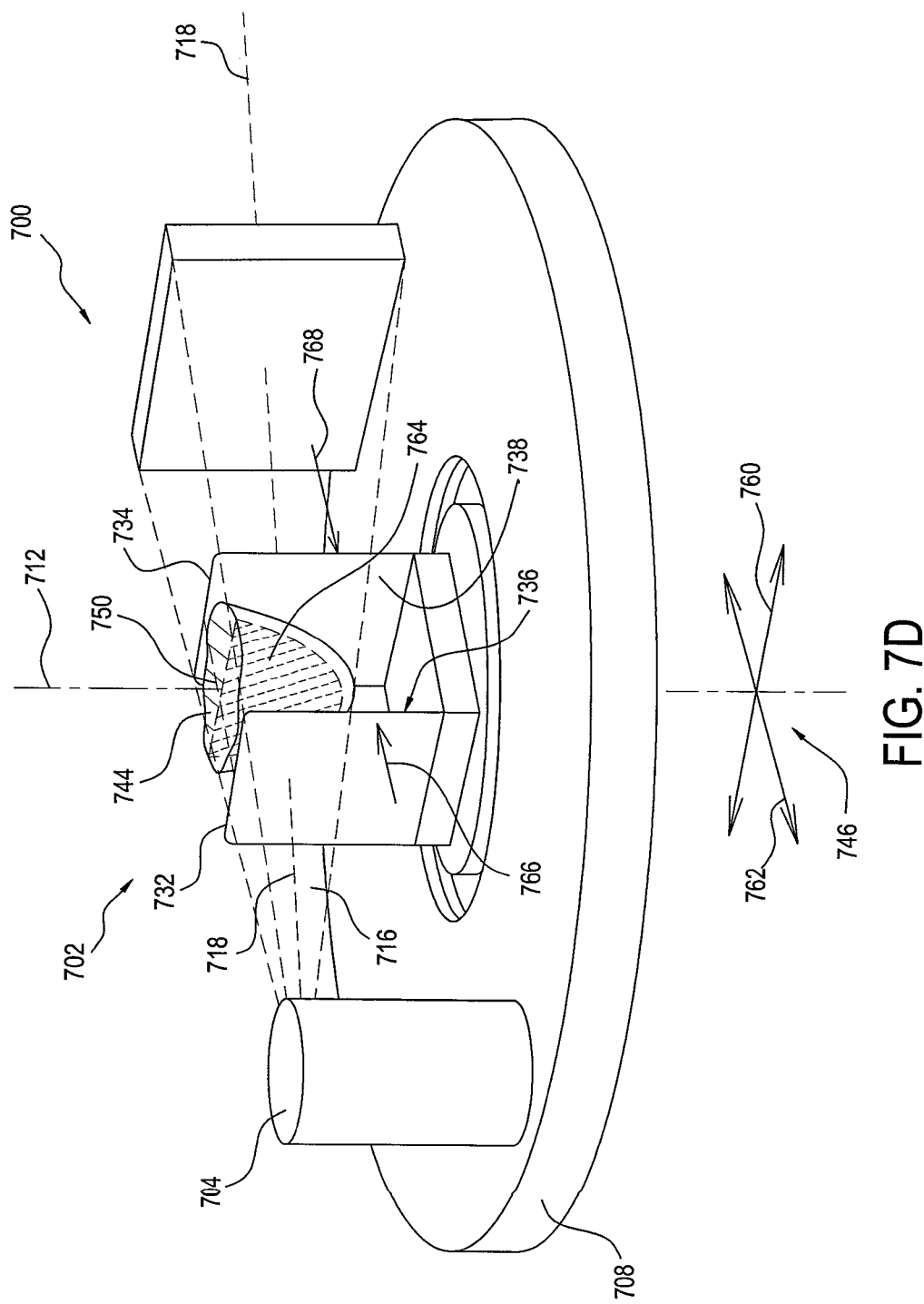
FIG. 7D shows, in schematic side elevation, a portion of an exemplary CBBCT imaging system including a stationary imaging subsystem prepared according to principles of the invention.

FIG. 7D shows in schematic perspective view, further aspects of CBBCT imaging system 700, including stationary imaging subsystem 702, according to principles of the invention.

Referring again to FIG. 7C, and the system 700 configuration illustrated therein, after stationary imaging in the FIG. 7C configuration—i.e. with x-ray beam longitudinal axis 718 disposed generally parallel to axis 760 of breast reference frame 746, the breast 744 is released by operating the translation apparatus of the stationary scan subsystem to withdraw first 732 and second 734 effector panels in directions 762 and 764 respectively.

After the breast 744 has been released by the effector panels, stationary scan subsystem 702 is rotated about axis of rotation 712 into the orientation illustrated in FIG. 7D. Likewise, gantry 708 is rotated into the orientation shown in FIG. 7D.

It will be appreciated by the reader that the rotation of stationary imaging subsystem 702 and gantry 708 may occur simultaneously, or maybe sequential with one or the other of the stationary imaging subsystem 702 and gantry 708 rotating first.

Upon completion of the indicated rotations, x-ray source 704 is configured as shown with a longitudinal axis 718 of an x-ray beam 716 generated by the x-ray source 704 disposed generally normal to respective breast contacting surfaces 736, 738 of effector panels 732, 734 respectively. Note, however, that x-ray beam longitudinal axis 718 is now disposed in a new orientation generally parallel to axis 762 of breast frame of reference (in contrast to its orientation parallel to axis 760, shown in FIG. 7C). Consequently, system 700 is configured to image breast 744 through cross-section 764 rather than cross-section 750.

In anticipation of this imaging, in certain embodiments, including processes and methods according to the invention, the translation mechanism of stationary imaging subsystem 702 is activated to urge effector panels 732, 734 in respective directions 766, 768 towards the breast 744.

Figure 7E:
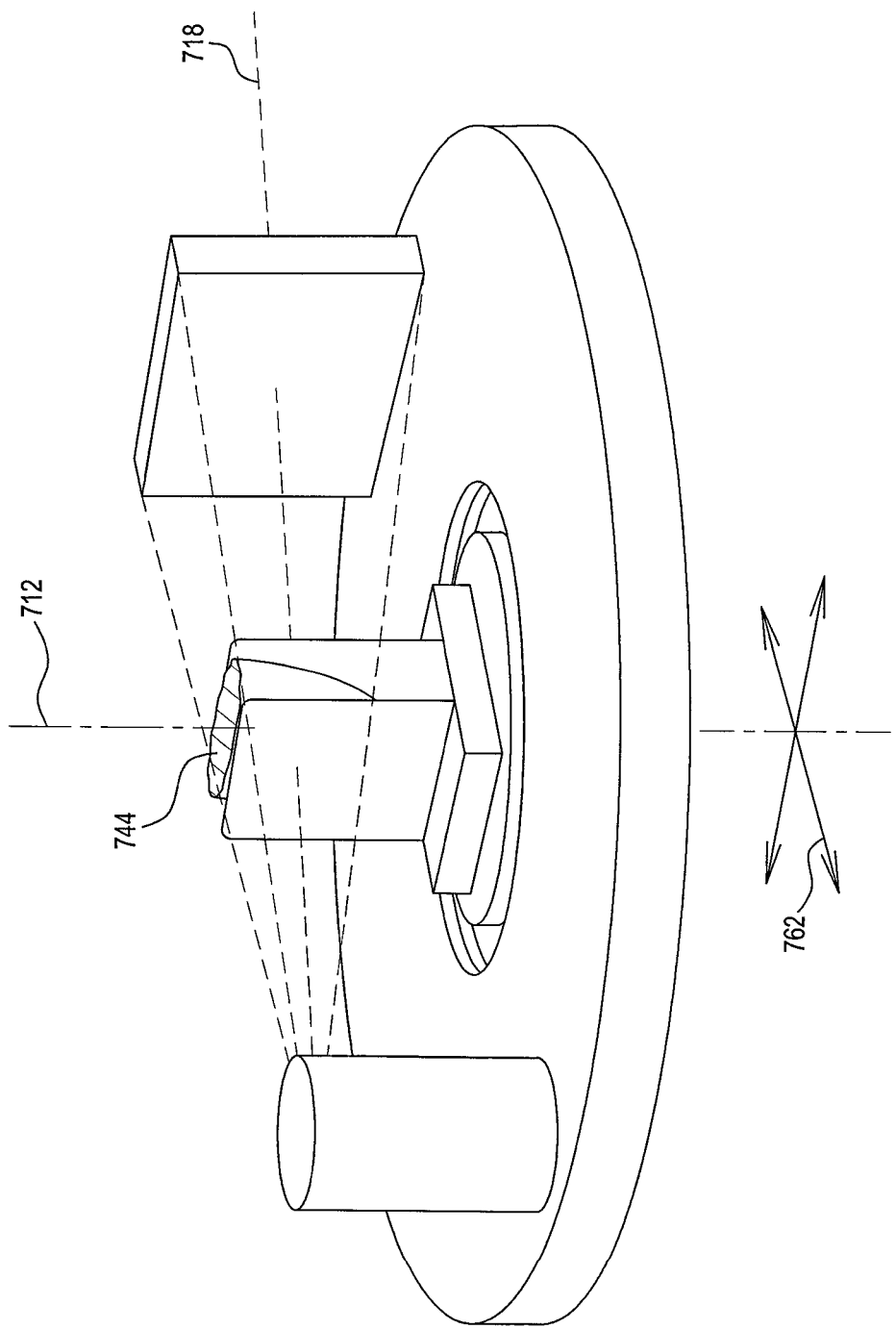
FIG. 7E shows, in schematic side elevation, a portion of an exemplary CBBCT imaging system including a stationary imaging subsystem prepared according to principles of the invention.

FIG. 7E thus shows system 700 with breast 744 compressed and ready for stationary imaging with the longitudinal axis 718 of x-ray beam 714 disposed parallel to axis 762.

In view of the foregoing, one of skill in the art will appreciate that in addition to performing CBBCT imaging of the breast, a system prepared according to the present invention will also be capable of performing one or more stationary scans in desired orientations with respect to a reference frame of the breast. Moreover, it will be possible to view the results of the stationary scans independently, or to employ those results by hybridization with CBBCT data to provide overall improvement in the CBBCT imaging results. Either or both of these applications will result in, among other benefits, improved imaging of calcifications and vascular structure within the breast.

It will be apparent to one of skill in the art that, in certain embodiments and aspects of the invention, the system will be simplified by employing effector panels including configurations and materials that are relatively transparent to the x-rays of the system. Accordingly, in certain embodiments of the invention, the effector panels will be disposed permanently in line with the x-ray beam of the system, i.e., in imaging configuration, rather than being disposed in a storage configuration when CBBCT scanning is operative and stationary scanning is not underway.

Figure 8:
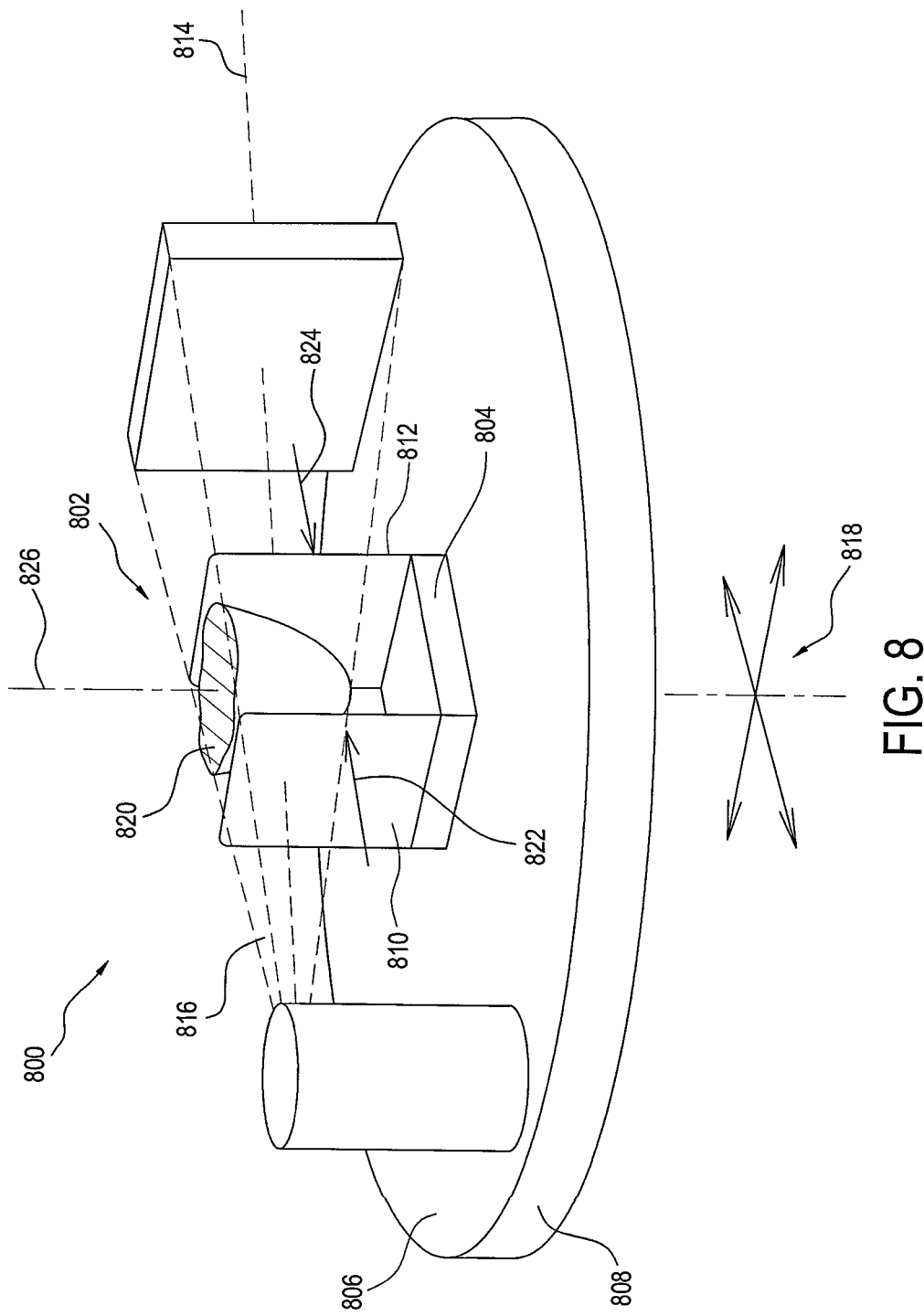
FIG. 8 shows, in schematic side elevation, a portion of an exemplary CBBCT imaging system including a stationary imaging subsystem prepared according to principles of the invention.

FIG. 8 illustrates one such exemplary system in which a CBBCT system 800 includes a stationary scan subsystem 802. A base 804 of the stationary scan subsystem is substantially permanently fixed to an upper surface 806 of a gantry 808, and rotates with the gantry at all times.

Accordingly, the system 800 of FIG. 8 has a gantry that does not require the aperture 724 of system 700. Nor is the rotary apparatus 726 of system 700 employed in system 800. Rather, the stationary scan subsystem 802 is permanently disposed with effector panels 810, 812 disposed generally transverse and generally normal to longitudinal axis 814 of x-ray beam 816 throughout both CBBCT scanning and stationary scan imaging.

When a stationary scan is desired gantry 808 is positioned and halted with longitudinal axis 814 disposed in a desired orientation with respect to the breast frame of reference 818. Thereafter, a translation mechanism within, for example, base 804 of the stationary scan subsystem 802 will be activated to urge effector panels 810 and 812 respectively inward towards the patient breast 820 and respective directions 822, 824. Once the breast has been contacted and, where appropriate, compressed, imaging will proceed in a manner consistent with the descriptions provided above.

Upon completion of the stationary scan, the translation mechanism reverses the motion of the effector panels to release the breast. Thereafter, additional rotation of the gantry 808 about axis of rotation 826 will permit additional CBBCT scans or reorientation of the system for additional stationary scans.

It will be appreciated by one of skill in the art that, throughout all of the embodiments described herewith, appropriate safety interlocks will be provided to ensure that release of the breast from any effector will be achieved prior to any motion of the gantry 808 or any stationary scan subsystem rotary apparatus. Such a safety interlock will be implemented as one or more of a mechanical interlock, an electromechanical interlock, and electromagnetic interlock, a pneumatic interlock, hydraulic interlock, or any other interlock effective and appropriate to the circumstances.

Figure 9:
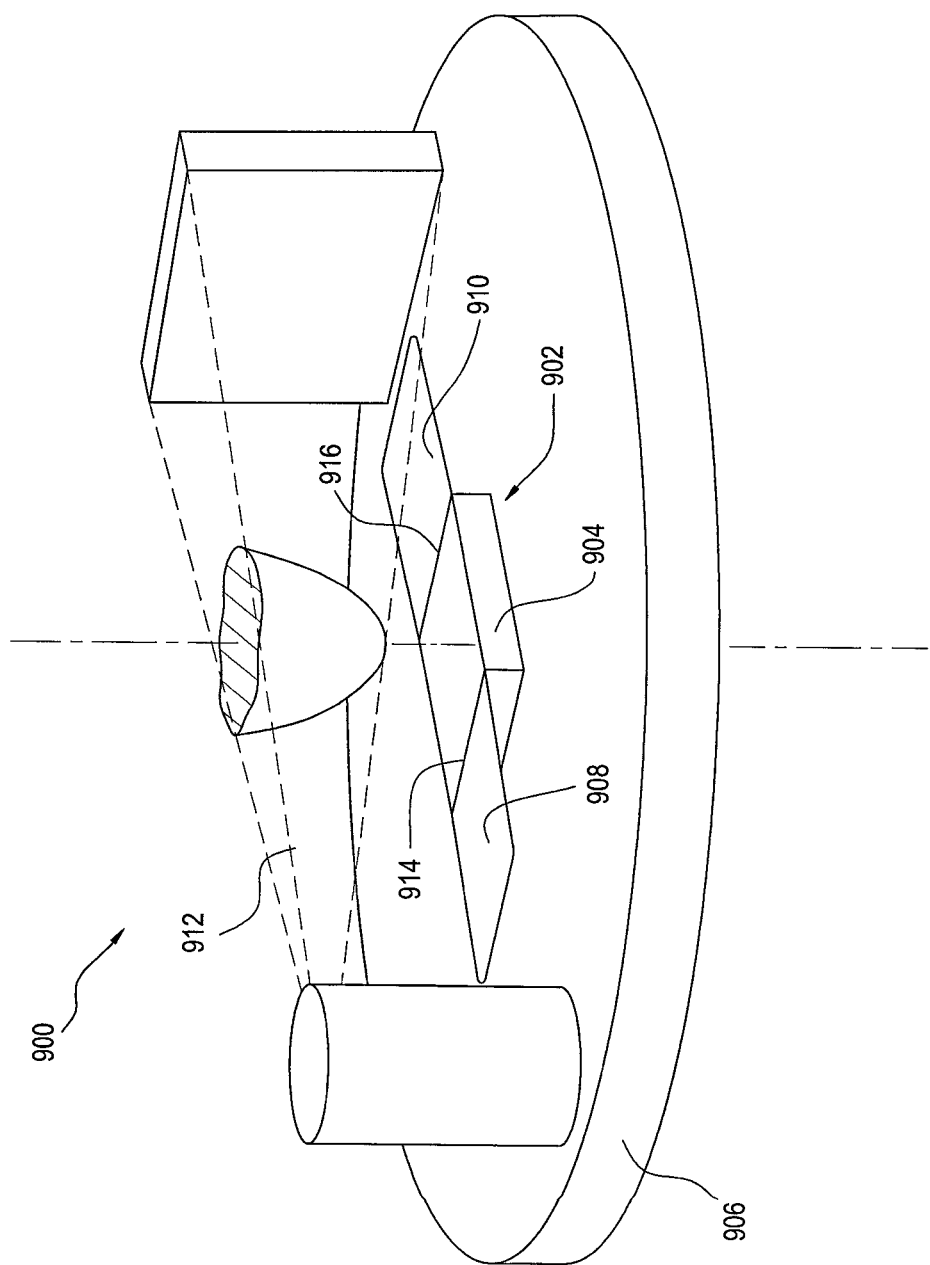
FIG. 9 shows, in schematic side elevation, a portion of an exemplary CBBCT imaging system including a stationary imaging subsystem prepared according to principles of the invention.

FIG. 9 shows in schematic perspective view, further aspects of CBBCT imaging system 900, including stationary imaging subsystem 902, prepared according to principles of the invention and disposed in a stationary imaging configuration.

System 900 is similar to system 800, described above, inasmuch as a base 904 of the stationary imaging subsystem 902 is disposed in substantially permanently fixed relation to the gantry 906. Stationary imaging subsystem 902 therefore rotates strictly synchronously with gantry 906 at all times.

Nevertheless, system 900 is unlike system 800 with respect to its effector panels. Unlike the effector panels 810, 812 of system 800, which are permanently disposed in line with the x-ray beam 816 such that the x-ray beam 816 impinges on the effector panels 810, 812 whenever the x-ray source is active, effector panels 908, 910 are configured to move out of the path of the x-ray beam 912 except when a stationary scan is undertaken.

Thus, in the illustrated embodiment, effector panels 908, 910, are pivotally coupled to base 904 at respective hinges 914, 916. In this way, the effector panels 908, 910 will be disposed in the illustrated storage configuration until stationary imaging is desired.

When stationary imaging is desired, the effector panels 908, 910 are adapted to pivot into an orientation such that they are disposed within the x-ray beam 912, and enter an imaging configuration similar in appearance to that of FIG. 8.

One of skill in the art will appreciate that this pivotal configuration of the effector panels 908, 910 will be accomplished in respective embodiments by corresponding pivotal mechanisms, whether magnetically, electrically, hydraulically, pneumatically, or otherwise automatically controlled, or by manual reconfiguration by technical or medical personnel.

It will also be appreciated that the pivotal mechanism illustrated is only one of a variety of mechanisms and arrangements available to place the stationary scan subsystem into a storage configuration. These mechanisms and arrangements will include, of course, the arrangement illustrated above in FIGS. 8A and 8B as well as a wide variety of other arrangements that will become apparent.

Figure 10:
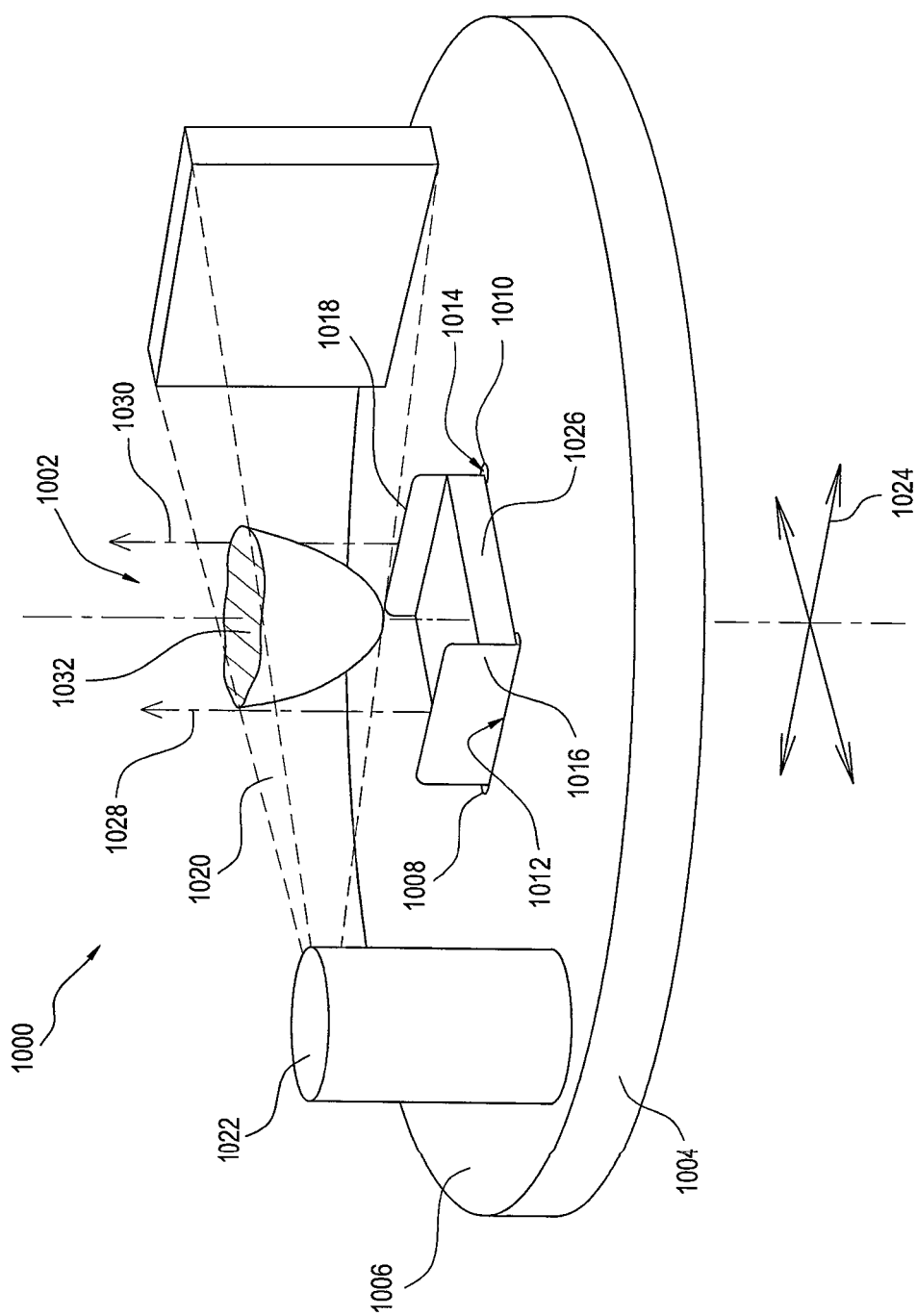
FIG. 10 shows, in schematic side elevation, a portion of an exemplary CBBCT imaging system including a stationary imaging subsystem prepared according to principles of the invention.

FIG. 10 shows, for example, in schematic perspective view, further aspects of CBBCT imaging system 1000, including stationary imaging subsystem 1002, prepared according to principles of the invention and disposed in a stationary imaging configuration.

Imaging system 1000 includes a gantry 1004 with an upper surface 1006. Upper surface 1006 includes first 1008 and second 1010 internal circumferential edges defining respective first 1012 and second 1014 recesses in the gantry 1004.

As will be apparent to the reader, recesses 1012 and 1014 are adapted to receive respective first 1016 and second 1018 effector panels therewithin such that the effector panels are disposed in a storage configuration. In the illustrated storage configuration, the effector panels 1016 and 1018 are disposed substantially out of the path of an x-ray beam 1020 produced by an x-ray source 1022 of system 1000 when the x-ray source is in operation.

It will be equally apparent that, when a stationary scan is desired, the gantry 1004 can be disposed in a desired orientation with respect to a breast frame of reference 1024. Accompanying this positioning, an appropriate mechanism disposed within a base 1026 of the stationary scan subsystem 1002 will correspondingly elevate the effector panels 1016 and 1018 by urging them in respective directions 1028, 1030. As such, the effector panels 1016 and 1018 will be disposed adjacent to the breast 1032 to be imaged in a configuration reminiscent of that shown in, for example, FIG. 7D. Thereafter, the effector panels will be urged inwardly towards the breast in a manner that will be well understood in light of the foregoing descriptions.

Of course, having read the present disclosure, and in hindsight, one of skill in the art will readily and immediately comprehend a wide variety of other approaches and mechanisms through the use of which, in corresponding embodiments of the invention, effector panels will be positioned in operative configurations and, alternately, positioned in a respective storage configurations. Likewise, one of skill in the art will readily appreciate that the particular implementations presented here are intended to be merely exemplary, and that the stationary imaging subsystem need not have a base, per se, but that any necessary mechanisms may be included integrally within the gantry, as part of a patient table, or otherwise in a manner to effect the desired operation of the effectors.

Figure 11:
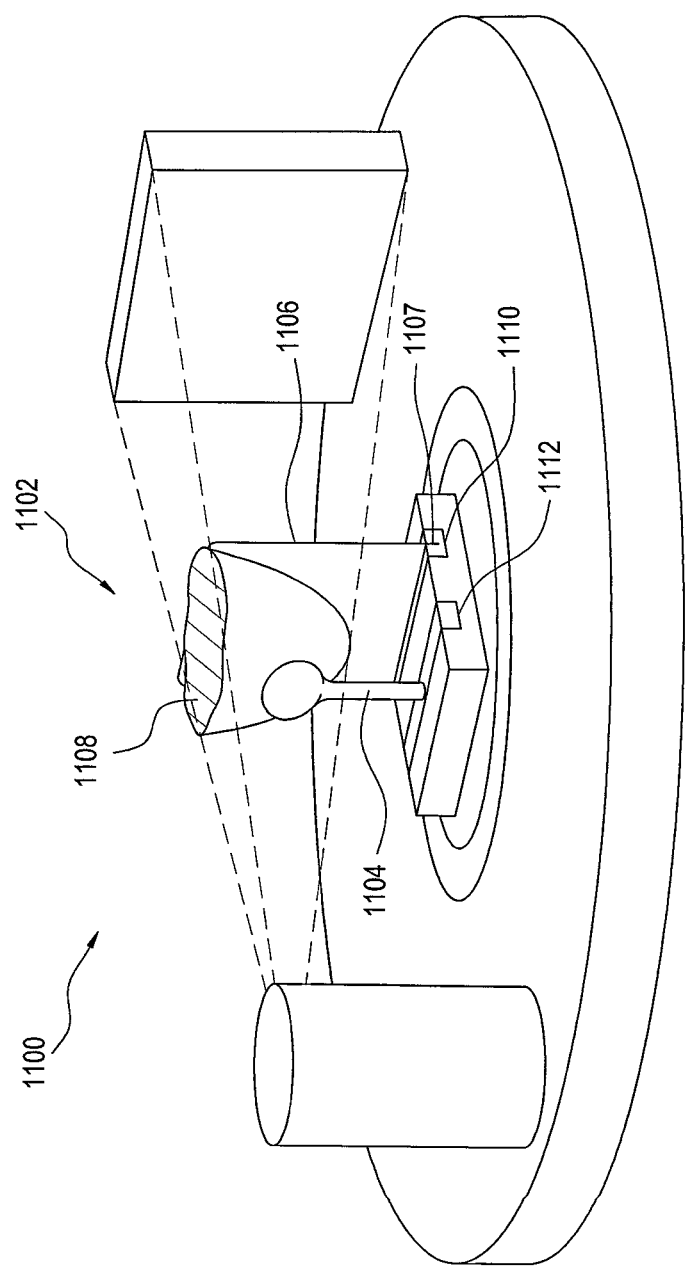
FIG. 11 shows, in schematic side elevation, a portion of an exemplary CBBCT imaging system including a stationary imaging subsystem prepared according to principles of the invention.

Moreover, the effectors need not be effector panels, as described and shown above, but may be any desirable configuration of an effector such as, for example, an effector wand as shown and described with respect to FIG. 11.

FIG. 11 shows, for example, in schematic perspective view, further aspects of CBBCT imaging system 1100, including stationary imaging subsystem 1102, prepared according to principles of the invention and disposed in a stationary imaging configuration.

Stationary imaging subsystem 1102 includes one effector wand 1104 and one effector panel 1106. It will be immediately apparent to the reader that a variety of effector wands will be employed in respective embodiments and applications of the invention to apply pressure to a selected region of the breast 1108 for improved imaging. It will also be immediately apparent that in certain embodiments, two effector wands will be employed rather than the illustrated single effector wand and single effector panel.

In the illustrated embodiment, the effector wand 1104 and effector panel 1106 include respective effector couplers, e.g., 1107. The effector coupler 1107 is adapted to be received within and coupled to a respective effector receiver e.g., 1110, 1112 of the stationary scan subsystem 1102. Accordingly, the effector couplers, e.g., 1107 and effector receiver 1110 combination serves to removably couple the effector, e.g. 1106, to the stationary scan subsystem 1102 for substantial support and positioning.

In still other embodiments of the invention, the stationary imaging subsystem will be adapted to receive, and operate with, any of a wide variety of effector wands and effector panels on a replaceable basis according to the requirements of a particular imaging situation. In still other aspects of the invention, selection and positioning of the effector, whether wand or panel, will be completed manually in certain embodiments, and automatically by corresponding mechanisms of the system 1100 in other embodiments.

In still further aspect of the invention, effector wands and effector panels will be rotated into position or elevated into position within the system according to the requirements of a particular patient imaging situation. In yet further aspects and embodiment of the invention, effector wands and effector panels will be delivered to their appropriate location within the imaging system from a cartridge installed into or disposed within the system. In still further aspects and embodiments of the invention, effector wands and effector panels will include biocompatible materials. In still further aspects and embodiments of the invention, effector wands and effector panels will be single use disposable, and in other embodiments and aspects of the invention, effector wands and effector panels will be readily sterilized.

Figure 12:
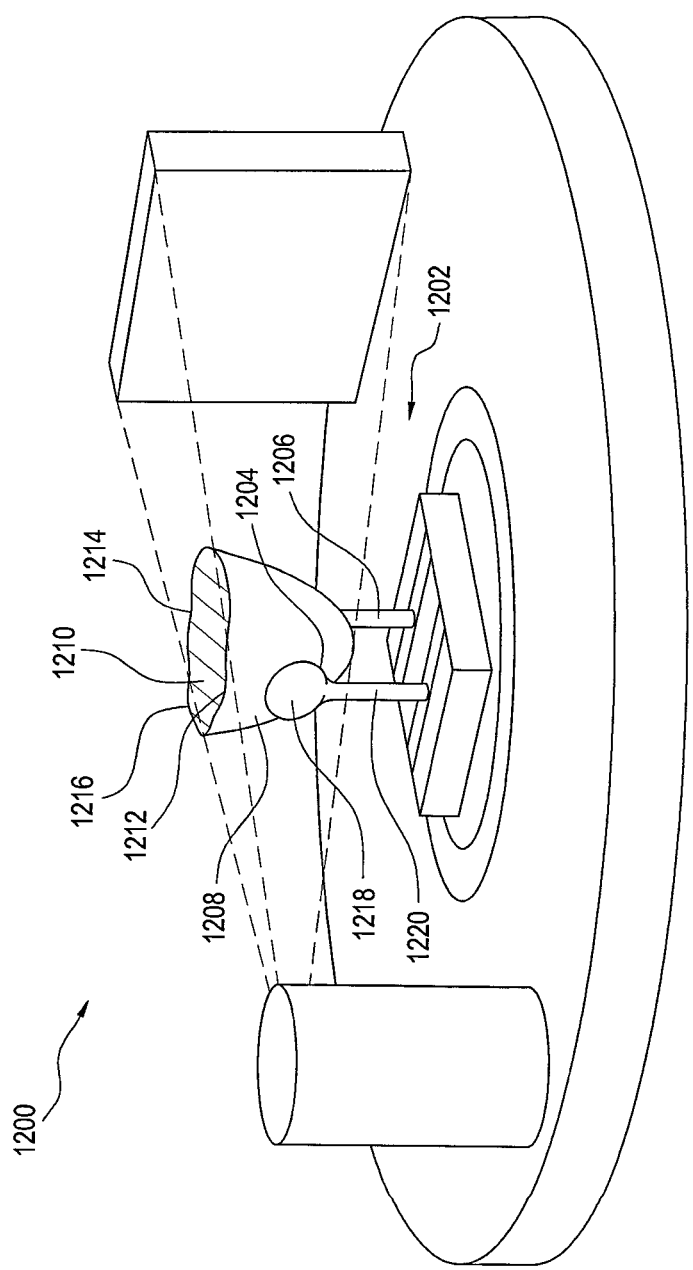
FIG. 12 shows, in schematic side elevation, a portion of an exemplary CBBCT imaging system including a stationary imaging subsystem prepared according to principles of the invention.

FIG. 12 shows, for example, in schematic perspective view, further aspects of CBBCT imaging system 1200, including stationary imaging subsystem 1202, prepared according to principles of the invention and disposed in a stationary imaging configuration.

Stationary imaging subsystem 1202 includes two effector wands 1204, 1206 disposed on opposite sides of the breast 1208 being imaged. A cross-section of the breast 1210 taken for illustrative purposes shows by the local curvature 1212, 1214 of its peripheral edge 1216 the relatively localized compression of the breast due to the localized contact between the effector wands, 1204, 1206 and the respective breast surface regions.

It will also be understood that an individual wand 1204 will be prepared having particular characteristics and parameters including, for example, the size and shape, degree of flexibility elasticity, flexibility and malleability of a shaft portion 1220 of the wand and likewise the size, shape, elasticity and rheology, of the head portion 1218 of the wand 1204.

In light of the foregoing, one of skill in the art will appreciate that, by the careful selection of effector elements, and their respective characteristics, a wide variety of desirable effects will be achieved in terms of breast stabilization and/or compression. Consequently improved imaging will be available according to the requirements of a particular patient or protocol.

Figure 13:
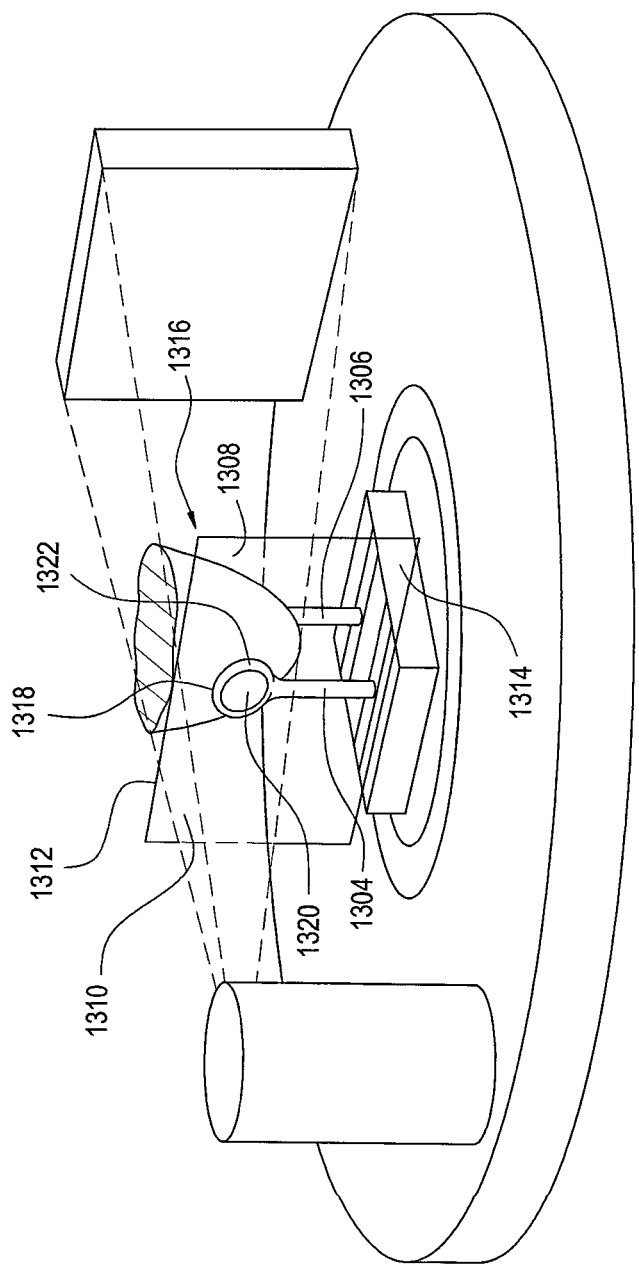
FIG. 13 shows, in schematic side elevation, a portion of an exemplary CBBCT imaging system including a stationary imaging subsystem prepared according to principles of the invention.

FIG. 13 shows, for example, in schematic perspective view, further aspects of CBBCT imaging system 1300, including stationary imaging subsystem 1302, prepared according to principles of the invention and disposed in a stationary imaging configuration.

Stationary imaging subsystem 1302 includes two effector wands 1304, 1306 and a shielding collimator 1308. The exemplary shielding collimator 1308 illustrated includes a relatively x-ray-opaque panel portion 1310 with an outer peripheral edge 1312. The shielding collimator 1308 has a proximal surface region 1314 disposed within the outer peripheral edge. A distal surface region 1316 of the shielding collimator 1308 is disposed in spaced relation to the proximal surface region 1314.

An inner peripheral edge 1318 of the proximal surface region 1314 surrounds and defines an aperture 1320 between the proximal surface region 1314 and the distal surface region 1316. In certain embodiments of the invention, a window of relatively x-ray transparent material is disposed within the aperture 1320.

In certain applications of the invention, as illustrated, the aperture 1320 is disposed in alignment with the head 1322 of the illustrated effector wand 1304.

In still other embodiments of the invention, the stationary imaging subsystem will be adapted to receive, and operate with, any of a wide variety of effector wands and effector panels on a replaceable basis according to the requirements of a particular imaging situation. In still other aspects of the invention, selection and positioning of the effector, whether wand or panel, will be completed manually in certain embodiments, and automatically by corresponding mechanism of the system 1300 in other embodiments.

FIGS. 14A-14D, show in schematic perspective view, a variety of exemplary effector wands and effector panels for an exemplary stationary imaging subsystem of a CBBCT imaging system, prepared according to principles of the invention.

Figure 14B:
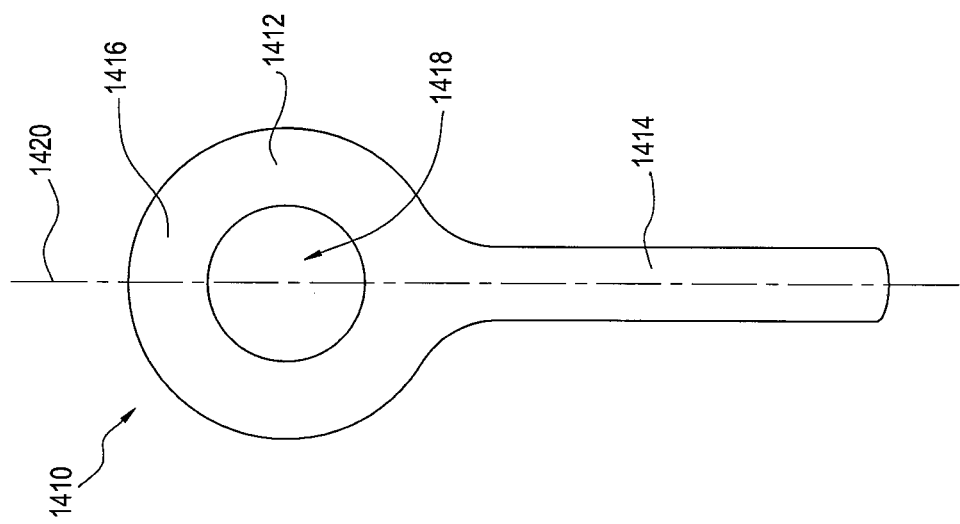
FIG. 14B shows, in schematic perspective view, a portion of an exemplary CBBCT imaging system including a further exemplary effector wand prepared according to principles of the invention.
Figure 14A:
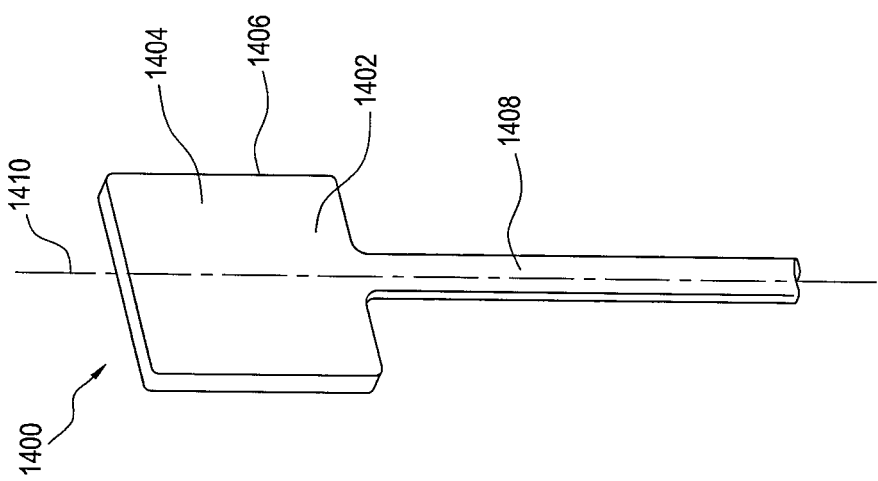
FIG. 14A shows, in schematic perspective view, a portion of an exemplary CBBCT imaging system including an exemplary effector wand prepared according to principles of the invention.

FIG. 14A shows an exemplary effector wand 1400 having a head portion 1402 with a patient contact surface region 1404. The patient contact surface region 1404 is generally planar, and has a generally rectangular peripheral edge 1406. The reader will note that this contrasts with the generally circular peripheral edge illustrated, e.g., in effector wand 1104 of FIG. 11.

Effector wand 1400 has a shaft portion 1408 coupled to the head portion 1402. In the illustrated embodiment, the shaft portion 1408 has a longitudinal axis 1410. A cross-section of the shaft portion 1408 taken transverse to the longitudinal axis 1410 is generally rectangular.

It will be noted, and particularly with reference to the following examples, that the patient contact surface region 1404 need not be planar and the cross-section of the shaft portion 1408 need not be rectangular. It should also be noted that the effector wand 1400, including the shaft 1408 and head 1402 of the effector wand 1400 will, in certain embodiments, be formed as an integral unit, and in other embodiments as an assembly of components.

FIG. 14B shows a further exemplary effector wand 1410 having a head portion 1412 and a shaft portion 1414. In effector wand 1410, the head portion 1412 includes a patient contact surface region 1416 that is generally toroidal in shape. Accordingly, the patient contact surface region 1416 defines an aperture 1418.

In the illustrated embodiment, the shaft portion 1414 has a longitudinal axis 1420. A cross-section of the shaft portion 1414 taken transverse to the longitudinal axis 1420 is generally circular. As noted above, however, in respective embodiments the cross-section will be rectangular, elliptical, or of any other geometry producing operative characteristics considered beneficial in the context of a particular embodiment, patient or protocol.

In certain embodiments of the invention, a window of relatively x-ray transparent material is disposed within the aperture 1418. In certain embodiments, it will be advantageous to include, in the balance of the effector wand, a material that is relatively x-ray-opaque. In other embodiments of the invention, the entirety of the wand/wand assembly will include a material that is relatively x-ray transparent.

In certain embodiments, the wand will include a material that is relatively flexible. In other embodiments of the invention, the wand will include a material that is relatively rigid. Accordingly, the overall characteristics of the embodiment will be selectable according to a particular design by the appropriate inclusion of materials that provide, for example, cushioning and/or deflection so as to increase patient comfort and other aspects of functionality that will be evident to one of ordinary skill in the art.

Figure 14D:
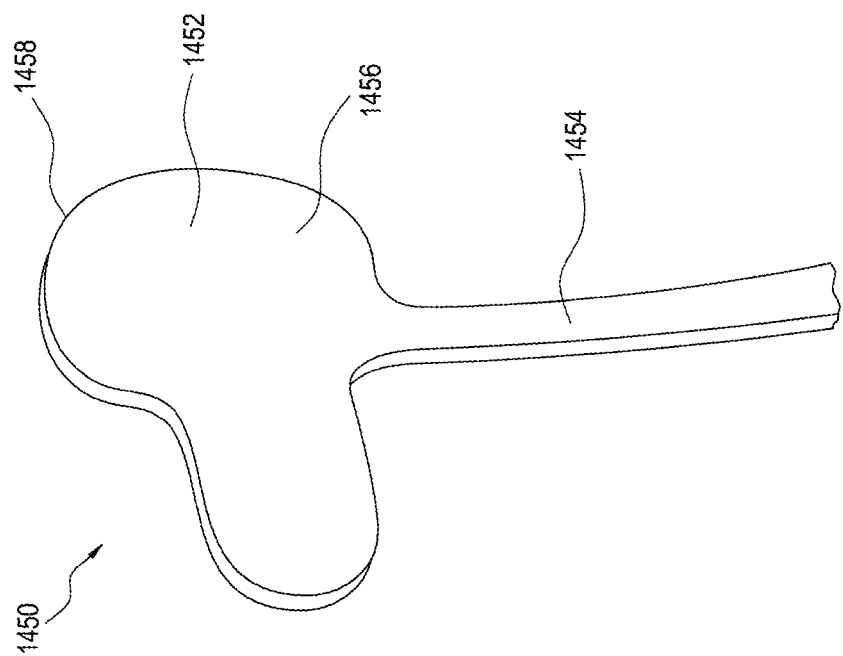
FIG. 14D shows, in schematic perspective view, a portion of an exemplary CBBCT imaging system including yet another exemplary effector wand prepared according to principles of the invention.
Figure 14C:
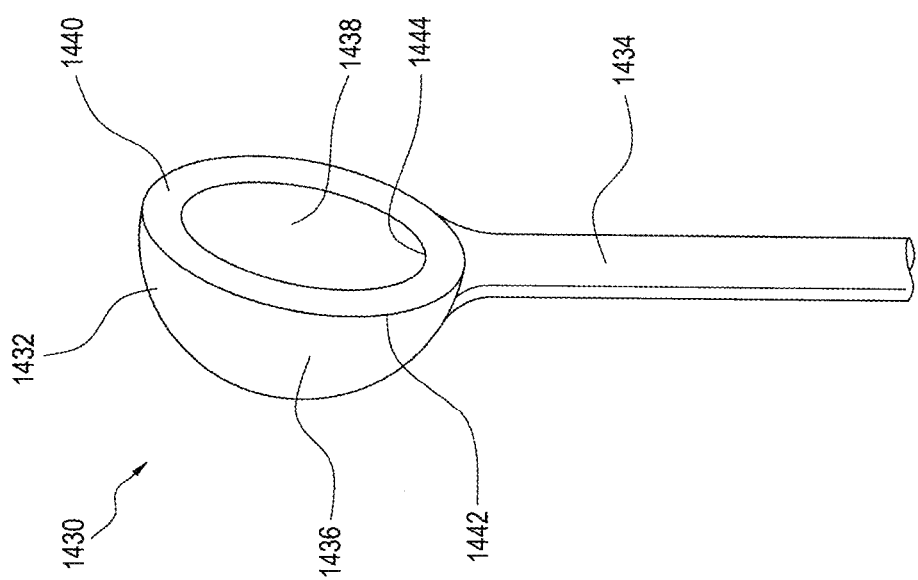
FIG. 14C shows, in schematic perspective view, a portion of an exemplary CBBCT imaging system including a still further exemplary effector wand prepared according to principles of the invention.

FIG. 14C shows still another exemplary effector wand 1430 having a head portion 1432 and a shaft portion 1434. In the illustrated embodiment, the head portion includes a first generally convex surface region 1436 and a second generally concave surface region 1438. A peripheral surface region 1440 is disposed between respective edges 1442, 1444 of the first surface region 1436 and second surface region 1438.

As illustrated, edges 1442 and 1444 are generally circular, and curved surface regions 1436, 1438 are generally hemispherical. It will be readily apparent in light of the present disclosure as a whole, that other shapes and forms will be used in corresponding embodiments of the invention.

In addition, in certain embodiments, surface region 1438 will be substantially planar, such that the region within circumferential edge 1442 is substantially a disk. Some such embodiments will include a generally solid material throughout the spatial region between surface regions 1436 and 1438. In other embodiments, there will be a cavity disposed between surface regions 1436 and 1438 which, in respective embodiments, will be evacuated, filled with air, or filled with another material having desirable characteristics.

It will be appreciated by one of skill in the art that either of surface region 1436 or 1438, or any combination thereof, will be employed as a patient contact surface region according to the requirements of a particular patient or protocol.

FIG. 14D shows still another exemplary effector wand 1450 having a head portion 1452 and a shaft portion 1454. The head portion 1452 includes a patient contact surface region 1456 with an external peripheral edge 1458. The illustrated peripheral edge has an arbitrary curvature. In light of the foregoing, it will be apparent that the external peripheral edge will have, in respective embodiments, any geometric form, or regular or irregular curve according to the requirements of a particular patient or protocol.

In addition, it is an aspect of the invention that, in certain embodiments of the invention, the form and/or curvature of the peripheral edge 1458, and of the contact surface region 1456 will be selected and/or prepared according to the requirements of a particular patient. Thus, for example, effector wand 1450 will be prepared having a edge curvature 1458 that is designed for a particular patient, based on parameters such as the presence and/or geometry of a region of interest within the breast to be imaged.

In certain aspects of the invention, this custom-prepared effector wand 1450 will be prepared using conventional mechanical machining processes. In other embodiments of the invention, the custom prepared effector will be molded, formed by consolidated powder processes, formed by electrochemical machining processes, formed by electrical discharge machining, formed by laser machining processes, formed by subtractive processes including, for example, lithographic or photolithographic processes, formed by additive processes including, for example, 3D printing of thermoplastic polymers, of laser sintered particles, of laser cured polymers, or by any other means or process appropriate to the requirements of the subject custom-prepared effector wand that are known or become known in the art, including combinations thereof.

Figure 15A:
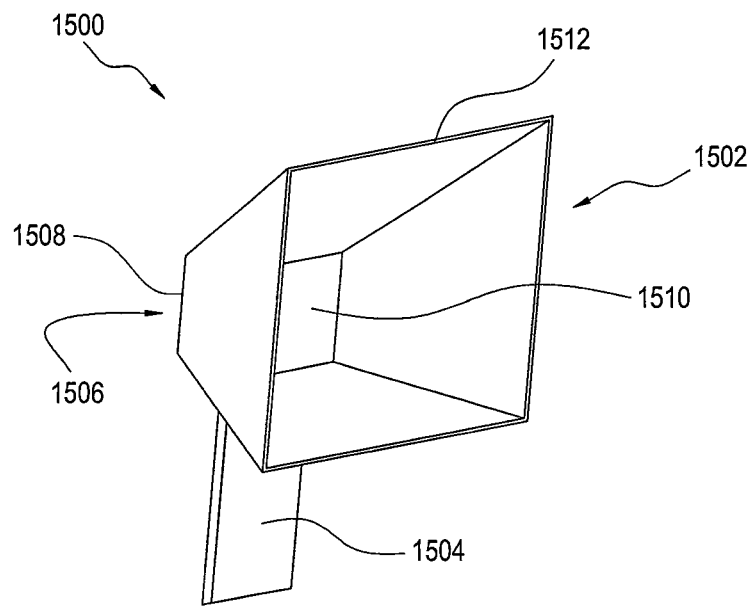
FIG. 15A shows, in schematic perspective view, a portion of an exemplary CBBCT imaging system including an effector with a collimator portion prepared according to principles of the invention.

FIG. 15A shows still another exemplary effector wand 1500 having a head portion 1502 and a shaft portion 1504. The head portion 1502 includes a patient contact proximal surface region 1506 with an external peripheral edge 1508. In the illustrated example, a distal surface region 1510 is disposed in generally parallel spaced relation to proximal surface region 1506.

In the exemplary embodiment illustrated, the peripheral edge 1508 is bordered by, and coupled to support, a generally pyramid shielding collimator 1512. The shielding collimator 1512 will, in exemplary embodiments, include a relatively x-ray opaque material and will serve to substantially reduce the passage of x-rays towards the breast being imaged, except within the area of the proximal surface region 1506.

As apparent from the figure, shielding collimator 1512 is generally concave when viewed from a distal perspective. However, one of skill in the art will appreciate that in other embodiments of the invention, the shielding collimator will be generally convex when viewed from a distal perspective. In still other embodiments of the invention, the shielding collimator will be substantially planar. In still further embodiments of the invention, the shielding collimator will have any shape as to its peripheral edge and surface regions as deemed beneficial according to the requirements of a particular patient or protocol.

Figure 15B:
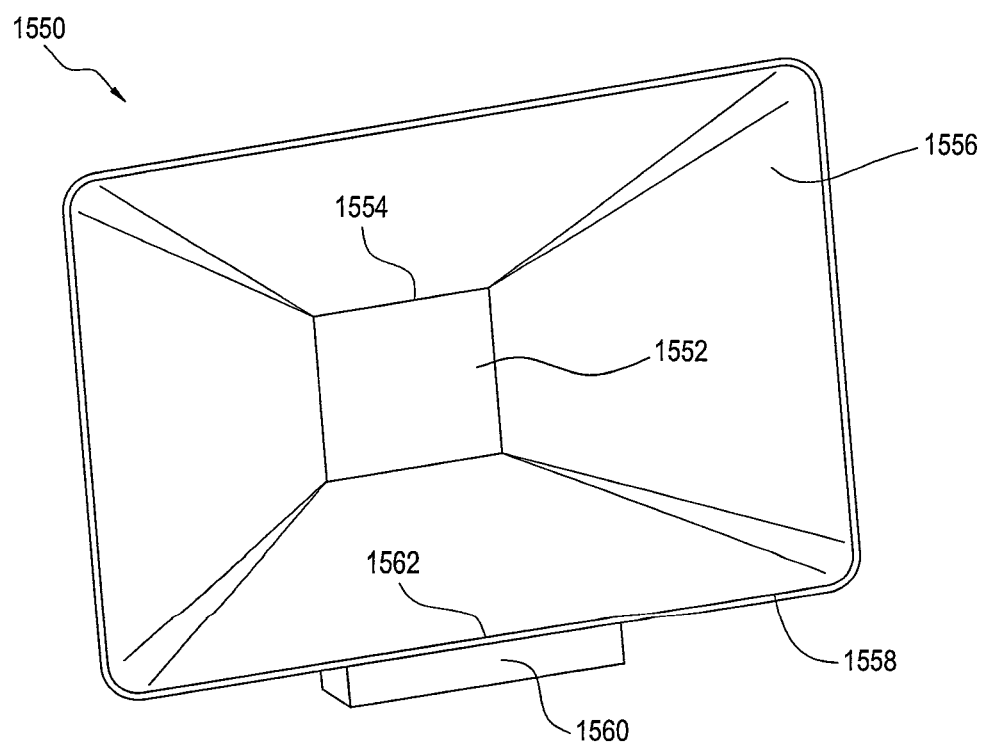
FIG. 15B shows, in schematic perspective view, a portion of an exemplary CBBCT imaging system including a further effector with a collimator portion prepared according to principles of the invention.

FIG. 15B shows yet another exemplary effector wand 1550 having a head portion 1552. The head portion 1552 includes an external peripheral edge 1554. The head portion 1552 is coupled at the external peripheral edge 1554 to a shielding collimator 1556. The shielding collimator has an external peripheral edge 1558, and includes a coupler 1560 at a lower portion 1562 of the external peripheral edge 1558.

The structural characteristics of the shielding collimator 1556 are such that, in certain embodiments of the invention, the coupler 1560 is directly coupled to a stationary scan subsystem of a CBBCT imaging system, and the shielding collimator serves to directly support head portion 1552 of the effector wand 1550. Accordingly, a discrete effector wand shaft portion is not required or necessarily present in such an embodiment.

One of skill in the art will appreciate that, while the exemplary effector 1550 illustrates a generally rectangular head portion 1552 and a generally pyramidal shielding collimator 1556, component or portions having any appropriate characteristics will be apparent from the present disclosure, and are accordingly deemed to be within its scope.

Figure 16:
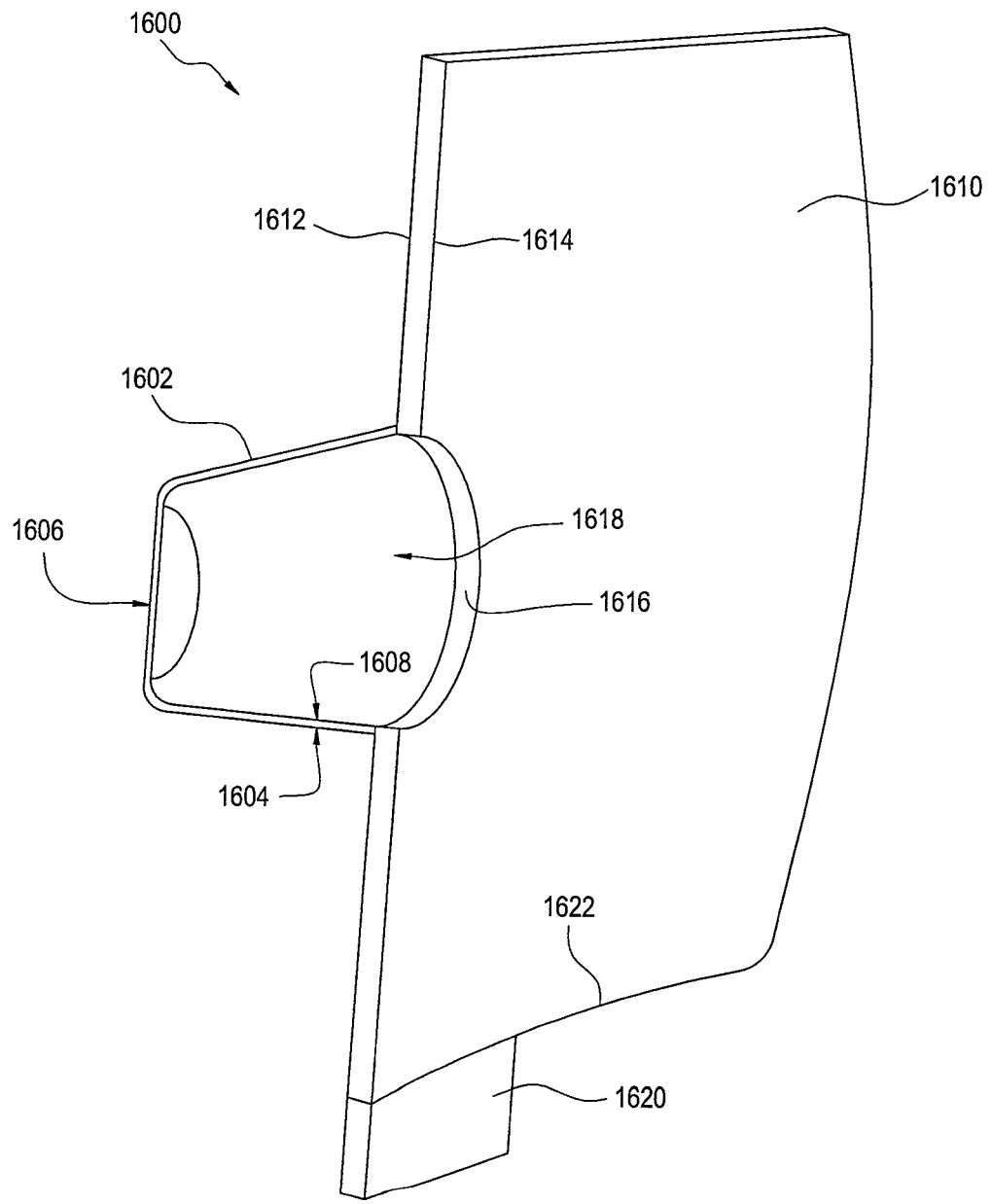
FIG. 16 shows, in schematic perspective view, a portion of an exemplary CBBCT imaging system including still another effector with a collimator portion prepared according to principles of the invention.

Thus, for example, FIG. 16 shows, in schematic sectional perspective view, an effector wand 1600 having a head portion 1602 with a generally convex proximal surface 1604 having a patient contacting surface region 1606. A generally convex distal surface region 1608 is disposed in spaced relation to the proximal surface 1604 region of the head portion 1602.

The effector wand 1600 includes a shielding collimator 1610 having a generally planar proximal surface region 1612. A generally planar distal surface region 1614 is disposed in generally parallel spaced relation to proximal surface region 1612. An internal circumferential edge 1616 of the proximal surface region 1612 defines an aperture 1618 through the shielding collimator 1610.

As illustrated, the head portion 1602 is coupled to the shielding collimator 1610 at the internal circumferential edge 1616, such that the head portion 1602 spans the aperture 1618 and is supported by the shielding collimator 1610.

A coupler 1620 is disposed at a lower outer peripheral edge region 1622 of the shielding collimator 1610, and serves to operatively couple the effector wand 1600 to a stationary scanning subsystem of a CBBCT imaging system. Once again, the structural characteristics of the shielding collimator 1610 are such that the shielding collimator serves to directly support the head portion 1602 of the effector wand 1600 when in operation. Accordingly, a discrete effector wand shaft portion is not required or necessarily present in such an embodiment.

Figure 17:
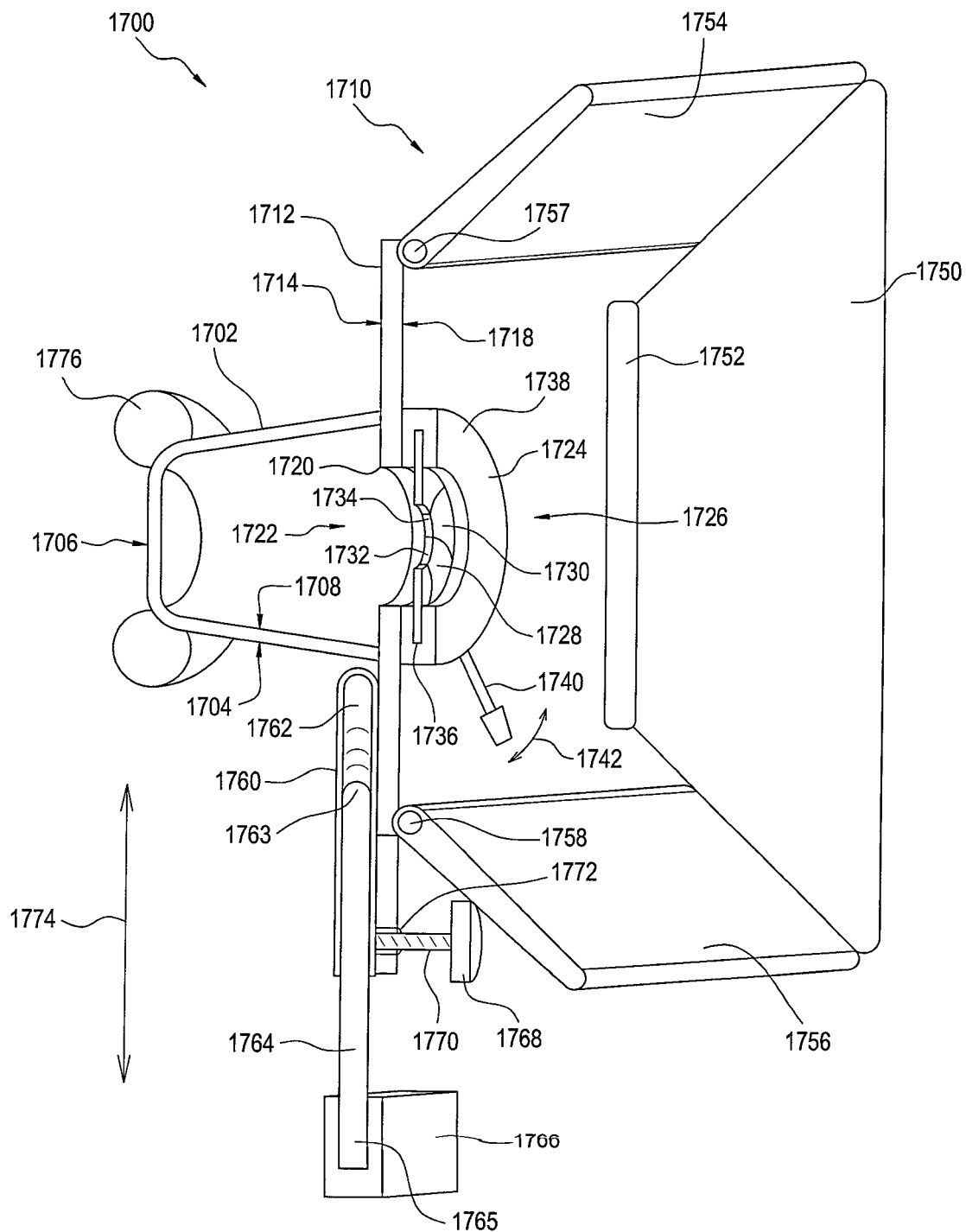
FIG. 17 shows, in schematic perspective view, a portion of an exemplary CBBCT imaging system including yet still another effector with a collimator portion prepared according to principles of the invention.

FIG. 17 shows, in schematic sectional perspective view, an effector wand 1700 having a head portion 1702. The head portion 1702 has a generally convex patient proximal surface region 1704 with a patient contacting surface region 1706. A generally convex distal surface region 1708 is disposed in spaced relation to the proximal surface region 1704 of the head portion 1702.

The effector wand 1700 includes a shielding collimator 1710. The shielding collimator 1710 includes a first body member 1712. The first body member 1712 has a generally planar proximal surface region 1714. A generally planar distal surface region 1718 is disposed in generally parallel spaced relation to proximal surface region 1714. An internal circumferential edge 1720 of the proximal surface region 1714 defines an aperture 1722 through the shielding collimator first body member 1712.

In the illustrated embodiment, a mechanical iris mechanism 1724 is coupled to the distal surface 1718 such that a central aperture 1726 of the mechanical iris mechanism 1724 is disposed generally coaxial with aperture 1722 of the first body member 1712.

In the exemplary embodiment illustrated, the mechanical iris mechanism and 1724 includes a plurality of leaf elements, e.g., 1728, 1730. The leaf elements have respective internal ends 1732, 1734 and respective external ends, e.g., 1736. The respective external ends, e.g., 1736, are coupled to and supported by an operative mechanism 1738. In the device mechanism illustrated, the operative mechanism 1738 includes an operating lever 1740.

As will be understood by one of skill in the art in light of the foregoing disclosure, and in light of the art of mechanical irises, and operator will urge the operating lever 1740 along a circumferential direction 1742 so as to adjust, and thereby enlarge and/or reduce a diameter of the iris central aperture 1726.

In the exemplary embodiment provided here, the shielding collimator includes a second additional body member 1750. The additional body member 1750 is coupled, for example, with a hinge 1752 to the first body member 1712. In respective embodiments of the invention, additional body members, e.g. 1754, 1756 will likewise be coupled with respective hinges 1757, 1758 the first body member 1712.

In respective embodiments of the invention, the hinges, e.g., 1752, 1757, 1758 will be adapted and configured to allow manual adjustment of the body members, e.g., 1750, 1754, 1756 while providing an amount of internal frictional resistance appropriate to maintain the respective body members in a particular spatial configuration to which they are adjusted.

As will be immediately understood by the reader of ordinary skill in the art, the body members, e.g., 1712, 1750, 1754, 1756 as well as the mechanical iris leaf elements, 1728, 1730 will include respective materials that, in certain embodiments and aspects of the invention will be substantially opaque to x-rays of the energy employed in the CBBCT imaging system.

In contrast, in certain embodiments and aspects of the invention, the head portion 1702 of the effector wand 1700 will include a material that is substantially transparent to x-rays of the indicated energy.

In a further aspect of the invention, the first body member 1712 will be operatively coupled to a receiver element 1760. The receiver element 1760 will, in the illustrated embodiment, include a cylindrical recess or bore 1762 therewithin.

An upper end 1763 and adjacent portion of the shaft element 1764 is adjustably disposed within the cylindrical recess or bore 1762 in the manner shown. A lower end 1765 of the shaft element 1764 includes a coupler 1766. The coupler 1766 is adapted and configured to interface with a complementary effector receiver portion of a stationary scanning subsystem of a CBBCT imaging system in the manner previously described (see, e.g, FIG. 11).

One of skill in the art will readily apprehend that by operation of an adjustment mechanism (shown here as an adjusting knob 1768 with a threaded shaft 1770 disposed within an internally threaded bore 1772), a height of the head portion 1702 of the effector wand 1700 will be adjusted upwardly or downwardly in direction (or degree of freedom) 1774. Accordingly, the patient contacting surface region 1706 of the head portion 1702 will be disposed adjacent to and placed into contact with a corresponding surface region of the breast to be imaged and, where beneficial, arranged to apply a level of pressure thereto corresponding to optimal imaging.

Thereafter, the hinged additional body members, e.g. 1750, 1754, 1756 of the shielding collimator will be adjusted to optimize shielding of the breast with respect to reducing x-ray exposure of the breast where such exposure is not necessary or beneficial.

In addition, other shielding elements, such as, for example, flexible shielding elements including adhesive, hook and loop, magnetic or other coupling mechanisms may be employed in certain embodiments of the invention so as to ensure complete coverage and avoid any gaps in the shielding provided by the shielding collimator 1710.

In a further aspect of the invention, in certain embodiments of the invention and elastic cushion element 1776 such as, for example, a toroidal elastic cushion element, will be coupled to and supported by an adjacent portion of proximal surface region 1704. The elastic cushion element 1776 will be adapted to compress elastically in contact with a corresponding surface region of a breast being imaged so as to increase patient comfort.

Figure 18:
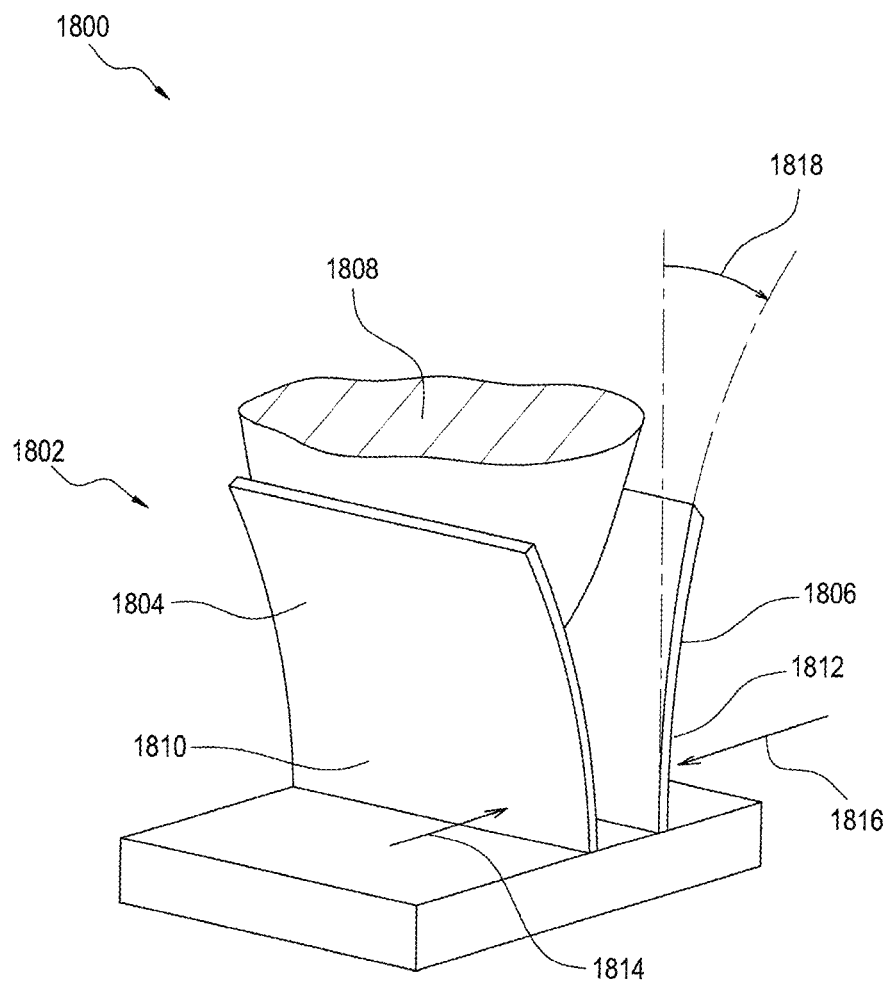
FIG. 18 shows, in schematic perspective view, a portion of an exemplary CBBCT imaging system including exemplary flexible effectors prepared according to principles of the invention.

FIG. 18 shows, in cross-sectional schematic perspective view, a portion 1800 of a CBBCT imaging system prepared according to principles of the invention including a stationary scan subsystem 1802 having relatively flexible effector panels e.g., 1804, 1806 like those described above in relation to element 324 and longitudinal axis 344 of FIG. 3.

As suggested by the figure, once the breast 1808 to be imaged is positioned between the effector panels 1804, 1806, respective lower regions 1810, 1812 of the effector panels 1804, 1806 are urged towards each other in respective directions 1814, 1816. As they contact the corresponding regions of the breast surface, they tend to deflect 1818 in a manner that optimizes breast support and compression with a minimum of patient discomfort.

In light of the foregoing disclosure, it will be apparent to one of skill in the art that the invention includes, among other aspects, a breast imaging system that has a CBBCT gantry. The CBBCT gantry includes an x-ray source and an x-ray detector. The x-ray source is adapted to produce a beam of x-rays, where the beam of x-rays has a beam longitudinal axis. It will be appreciated that the gantry has a first axis of rotation.

The breast imaging system also includes a rotary apparatus, where the rotary apparatus has an upper surface. The rotary apparatus has a second axis of rotation. The second axis of rotation is disposed substantially coincident with the first axis of rotation.

The breast imaging system also has a stationary scanning subsystem. The stationary scanning subsystem is coupled to and supported by the upper surface of the rotary apparatus, and the stationary scanning subsystem includes a first effector receiver and a second effector receiver. The first and second effector receivers are adapted to receive respective couplers of respective effectors. It will be understood that the effectors may be effector panels, effector wands, or other effectors as will be apparent in light of the totality of the present disclosure.

In certain embodiments, the breast imaging system also includes a controller. The controller is adapted, during a first time period, to synchronize a first rotation of the rotary apparatus with a second rotation of the CBBCT gantry such that an operational axis (see, e.g., FIG. 7) of the stationary scanning subsystem is disposed transverse to the beam longitudinal axis. The controller being adapted, during a second time period, to arrest the first rotation of the CBBCT gantry, and to arrest the second rotation of the stationary scanning subsystem with the operational axis of the stationary scanning subsystem substantially aligned with the beam longitudinal axis.

In certain embodiments of the invention, the controller includes a mechanical latch, the mechanical latch being removably and operatively coupled between the CBBCT gantry and the rotary apparatus. In some embodiments and aspects the mechanical latch is operatively coupled to an actuator. One of skill in the art will appreciate that in certain embodiments, the actuator is signalingly coupled to the controller, whereby the controller is adapted to control the operation of the mechanical latch. The actuator includes, in respective embodiments, a linear actuator and/or a rotary actuator.

It will also be understood that the invention includes a method for operating a breast imaging system that includes providing a CBBCT breast imaging system along with a stationary scan subsystem. The CBBCT breast imaging system and the stationary scan subsystem are, in certain embodiments, respectively supported for mutual rotation about a common axis of rotation.

In one step, the method includes rotating the CBBCT breast imaging system and the stationary scan subsystem synchronously while capturing a CBBCT scan of a breast. In a further step of the invention, the method includes halting the rotation of the CBBCT breast imaging system. In yet another step of the invention, the method includes orienting and positioning the stationary scan subsystem to support the breast being imaged, and thereafter capturing a stationary scan of the breast.

A method according to the invention will also include, in certain embodiments, the steps of producing a first three-dimensional voxel image of the breast based on the CBBCT scan, and producing a second two-dimensional pixel image of the breast based on the stationary scan.

A method according to the invention will also include, in certain embodiments, the still further steps of producing a combined image of the breast based on a combination of the CBBCT scan and the stationary scan.

In another aspect, the invention will include preparing a breast imaging system that includes a CBBCT gantry, where the CBBCT gantry is configured and adapted to rotate about an axis of rotation. The breast imaging system will include, in respective embodiments, an x-ray source that is adapted to produce a beam of x-rays. The beam of x-rays will have a longitudinal axis. The x-ray source is operatively coupled to the CBBCT gantry. Also operatively coupled to the gantry is an x-ray detector. The breast imaging system also includes a stationary scan subsystem that is operatively coupled to the CBBCT gantry.

The stationary scan subsystem includes a first effector, a second effector, and a base portion. The first effector is coupled to the base portion at a first displacement device and the second effector is coupled to the base portion at a second displacement device. The first and second displacement devices are adapted to reposition the first and second effectors respectively into a first operative state (in which the effectors are disposed within the beam of x-rays) and a second storage state (in which the first and second effectors are disposed outwardly of the beam of x-rays).

In certain aspects of the invention, the first displacement device includes a hinge and the first effector is disposed outwardly of the beam of x-rays by a pivotal motion of the hinge. Similarly, in some implementations of the invention, the first displacement device includes a linear actuator and the first effector is disposed outwardly of the beam of x-rays by a linear motion of the first effectors, e.g., into a recess.

The invention also includes, in certain aspects and embodiments, a method of operating a breast imaging system that includes the steps of: providing a CBBCT gantry; providing an x-ray source, the x-ray source being adapted to produce a beam of x-rays, the x-ray source being operatively coupled to the CBBCT gantry; providing an x-ray detector, the x-ray detector being operatively coupled to the CBBCT gantry; providing a stationary scan subsystem, the stationary scan subsystem including first and second effectors; rotating the CBBCT gantry about an axis of rotation and producing a first beam of x-rays from the x-ray source while detecting the first beam of x-rays at the x-ray detector to capture CBBCT image data during a first time interval; and halting the CBBCT gantry at a specific orientation and producing a second beam of x-rays from the x-ray source while detecting the second beam of x-rays at the x-ray detector to capture static image data during a second time interval.

In additional embodiments, the method includes the steps of disposing the first and second effectors outwardly of the first x-ray beam during the first time interval; and disposing the first and second effectors within the second x-ray beam during the second time interval. In still further embodiments, the inventive method includes the steps of disposing the first and second effectors within the second x-ray beam by rotating the stationary scan subsystem about the axis of rotation. In yet still further embodiments, the method includes the steps of disposing the first and second effectors within the second x-ray beam by pivoting the first and second effectors about respective first and second hinges.

Other embodiments of the invention include disposing the first and second effectors within the second x-ray beam by withdrawing the first and second effectors from respective recesses; and still other embodiments include disposing a shielding collimator within the second x-ray beam during the second time interval.

Further embodiments of the method according to the invention include disposing a shielding collimator between the x-ray source and the first and second effectors during the second time interval, and also adjusting a position of the shielding collimator with respect to the x-ray source during a third time interval, where the third time interval is disposed chronologically between the first time interval and the second time interval.

The same method also includes, in certain embodiments, adjusting a diameter of an aperture of the shielding collimator during the third time interval, the third time interval being disposed, chronologically, between the first time interval and the second time interval. It will be appreciated that where the aperture is circular, the diameter will relate directly to area. In other shapes of aperture, however, this will not hold true. Accordingly, in certain embodiments of the invention the method will also specifically include adjusting an areal dimension of an aperture of the shielding collimator during the third time interval, the third time interval disposed chronologically between the first time interval and the second time interval.

In additional aspects, the inventive method includes adjusting a position of the x-ray detector with respect to the x-ray source during the third time interval, the third time interval disposed chronologically between the first time interval and the second time interval.

Moreover, in yet further aspects, the stationary scan subsystem is substantially fixedly coupled to the CBBCT gantry. Accordingly, in some embodiments of the invention, the method includes having the stationary scan subsystem substantially pivotally coupled to the CBBCT gantry through respective bearings of the stationary scan subsystem and the CBBCT gantry, where the respective bearings are arranged for substantially coaxial rotation with respect to one another.

It will also be appreciated by one of skill in the art that, while the foregoing description has employed, for exemplary purposes, a CBBCT system having a generally circular gantry rotating in a substantially horizontal plane about a substantially vertical axis of rotation, the features of the present invention will readily be applied in a CBBCT system employing any other arrangement such as, for example, a gantry rotating in a substantially vertical plane about a substantially horizontal axis of rotation. Again, this being merely exemplary where any other orientation of gantry, or gantry arrangement such as, for example, a tubular truss gantry, or any other arrangement suggested by the present disclosure is also intended to fall within the scope of the present disclosure.

While the exemplary embodiments described above have been chosen primarily from the field of apparatus, and corresponding systems and methods, for secondary imaging during the operation of a CBBCT imaging system, including stationary scan imaging, one of skill in the art will appreciate that the principles of the invention are equally well applied, and that the benefits of the present invention are equally well realized in a wide variety of other imaging technologies, for example, imaging of other body parts and imaging of other subjects such as industrial and technological products. Further, while the invention has been described in detail in connection with the presently preferred embodiments, it should be readily understood that the invention is not limited to such disclosed embodiments. Rather, the invention can be modified to incorporate any number of variations, alterations, substitutions, or equivalent arrangements not heretofore described, but which are commensurate with the spirit and scope of the invention. Accordingly, the invention is not to be seen as limited by the foregoing description, but is only limited by the scope of the appended claims.

The invention claimed is:

1. A breast imaging system comprising:
   a Cone Beam Breast Computed Tomography (CBBCT) gantry, said CBBCT gantry including an x-ray source and an x-ray detector, said x-ray source being adapted to produce a beam of x-rays, said beam of x-rays having a beam longitudinal axis, said CBBT gantry having a first axis of rotation;
   a rotary apparatus, said rotary apparatus having an upper surface, said rotary apparatus having a second axis of rotation, said second axis of rotation being disposed substantially coincident with said first axis of rotation;
   a stationary scanning subsystem, said stationary scanning subsystem coupled to and supported by said upper surface, said stationary scanning subsystem including a first effector receiver and a second effector receiver, said first and second effector receivers being adapted to receive respective couplers of respective effectors; and
   a controller, said controller being adapted, during a first time period, to synchronize a first rotation of said rotary apparatus with a second rotation of said CBBCT gantry such that an operational axis of said stationary scanning subsystem is disposed transverse to said beam longitudinal axis, said controller being adapted, during a second time period, to arrest said second rotation of said CBBCT gantry, and arrest said first rotation of said stationary scanning subsystem with said operational axis of said stationary scanning subsystem substantially aligned with said beam longitudinal axis
wherein said controller includes a mechanical latch, said mechanical latch being removably and operatively coupled between said CBBCT gantry and said rotary apparatus.

2. A breast imaging system as defined in claim 1 wherein said mechanical latch is operatively coupled to an actuator.

3. A breast imaging system as defined in claim 2 wherein said actuator is signalingly coupled to said controller, whereby said controller is adapted to control an operation of said mechanical latch.

4. A breast imaging system as defined in claim 2 wherein said actuator includes a linear actuator.

5. A breast imaging system as defined in claim 2 wherein said actuator includes a rotary actuator.

6. A breast imaging system comprising:
   a Cone Beam Breast Computed Tomography (CBBCT) gantry, said CBBCT gantry being configured and adapted to rotate about an axis of rotation;
   an x-ray source, said x-ray source being adapted to produce a beam of x-rays, said beam of x-rays having a longitudinal axis, said x-ray source being operatively coupled to said CBBCT gantry;
   an x-ray detector, said x-ray detector being operatively coupled to said CBBCT gantry; and
   a stationary scan subsystem, said stationary scan subsystem being operatively coupled to said CBBCT gantry, said stationary scan subsystem including a first effector, a second effector, and a base portion, said first effector being coupled to said base portion at a first displacement device, said second effector being coupled to said base portion at a second displacement device, said first and second displacement devices being adapted to reposition said first and second effectors respectively in a first operative state in which said effectors are disposed within said beam of x-rays and a second storage state in which said first and second effectors are disposed outwardly of said beam of x-rays wherein said first displacement device comprises a hinge, and wherein said first effector is disposed outwardly of said beam of x-rays by a pivotal motion of said hinge.

7. A breast imaging system as defined in claim 6 wherein said first displacement device comprises a linear actuator, and wherein said first effector is disposed outwardly of said beam of x-rays by a linear motion of said first effector into a recess.

8. A method of operating a breast imaging system comprising:
   providing a Cone Beam Breast Computed Tomography (CBBCT) gantry;
   providing an x-ray source, said x-ray source being adapted to produce a beam of x-rays, said x-ray source being operatively coupled to said CBBCT gantry;
   providing an x-ray detector, said x-ray detector being operatively coupled to said CBBCT gantry;
   providing a stationary scan subsystem, said stationary scan subsystem including first and second effectors;
   rotating said CBBCT gantry about an axis of rotation and producing a first beam of x-rays from said x-ray source while detecting said first beam of x-rays at said x-ray detector to capture CBBCT image data during a first time interval; and
   halting said CBBCT gantry at a specific orientation and producing a second beam of said x-rays from said x-ray source while detecting said second beam of x-rays at said x-ray detector to capture static image data during a second time interval;
   disposing said first and second effectors outwardly of said first x-ray beam during said first time interval; and
   disposing said first and second effectors within said second x-ray beam during said second time interval.

9. A method of operating a breast imaging system as defined in claim 8, wherein said disposing said first and second effectors within said second x-ray beam comprises rotating said stationary scan subsystem about said axis of rotation.

10. A method of operating a breast imaging system as defined in claim 8, wherein said disposing said first and second effectors within said second x-ray beam comprises pivoting said first and second effectors about respective first and second hinges.

11. A method of operating a breast imaging system as defined in claim 8, wherein said disposing said first and second effectors within said second x-ray beam comprises withdrawing said first and second effectors from respective recesses.

12. A method of operating a breast imaging system comprising:
    providing a Cone Beam Breast Computed Tomography (CBBCT) CBBCT gantry;
    providing an x-ray source, said x-ray source being adapted to produce a beam of x-rays, said x-ray source being operatively coupled to said CBBCT gantry;
    providing an x-ray detector, said x-ray detector being operatively coupled to said CBBCT gantry;
    providing a stationary scan subsystem, said stationary scan subsystem including first and second effectors;
    rotating said CBBCT gantry about an axis of rotation and producing a first beam of x-rays from said x-ray source while detecting said first beam of x-rays at said x-ray detector to capture CBBCT image data during a first time interval;
    halting said CBBCT gantry at a specific orientation and producing a second beam of said x-rays from said x-ray source while detecting said second beam of x-rays at said x-ray detector to capture static image data during a second time interval; and
    disposing a shielding collimator within said second x-ray beam during said second time interval.

13. A method of operating a breast imaging system as defined in claim 12, wherein said disposing a shielding collimator within said second x-ray beam during said second time interval further comprises disposing said shielding collimator between said x-ray source and said first and second effectors during said second time interval.

14. A method of operating a breast imaging system as defined in claim 13, further comprising adjusting a position of said shielding collimator with respect to said x-ray source during a third time interval, said third time interval disposed chronologically between said first time interval and said second time interval.

* * * * *